United States Patent
Krissansen et al.

(10) Patent No.: US 7,192,931 B2
(45) Date of Patent: Mar. 20, 2007

(54) TREATMENT OF DEMYELINATING DISEASES

(75) Inventors: Geoffrey Wayne Krissansen, Auckland (NZ); Jagat Rakesh Kanwar, Auckland (NZ)

(73) Assignee: Neuren Pharmaceuticals Ltd., Auckland (NZ)

( * ) Notice: Subject to any disclaimer, the term of this patent is extended or adjusted under 35 U.S.C. 154(b) by 513 days.

(21) Appl. No.: 10/398,876

(22) PCT Filed: Oct. 11, 2001

(86) PCT No.: PCT/US01/32198

§ 371 (c)(1),
(2), (4) Date: Sep. 22, 2003

(87) PCT Pub. No.: WO02/30448

PCT Pub. Date: Apr. 18, 2002

(65) Prior Publication Data

US 2004/0053850 A1    Mar. 18, 2004

(30) Foreign Application Priority Data

Oct. 12, 2000 (NZ) ..................................... 507478

(51) Int. Cl.
*A61K 38/05* (2006.01)
*A61K 31/66* (2006.01)
*A61K 31/498* (2006.01)

(52) U.S. Cl. ................. 514/18; 514/114; 514/221; 514/234.2; 514/248; 514/249; 514/250; 514/378

(58) Field of Classification Search ..................... None
See application file for complete search history.

(56) References Cited

FOREIGN PATENT DOCUMENTS

WO    WO 95/17204    *    6/1995
WO    WO 00 01376 A    1/2000

OTHER PUBLICATIONS

Smith et al., Jan. 2000, Nature Medicine, vol. 6, No. 1, pp. 62-66.*
Guan et al., Mar. 2000, Brain Research, vol. 859, No. 2, pp. 286-292.*
Smith, et al.: "Autoimmune encephalomyelitis ameliorated by AMPA antagonists", Nature Medicine. U.S. Jan. 2000, vol. 6, No. 1. pp 62-66.
Guan, J., et al: "N-terminal tripeptide of IGF-1 (GPE) prevents the loss of TH positive neurons after 6-OHDA induced nigral lesion in rats.", Brain Research, Netherlands Mar. 24, 2000, vol. 859, No. 2. pp. 286-292.
Kanwar, J.R., et al: "Beta7 integrins contribute to demyelinating disease of the central nervous system.", Journal of Neuroimmunology. Netherlands Mar. 1, 2000, vol. 103, No. 2 pp. 146-152.

* cited by examiner

*Primary Examiner*—B. Dell Chism
(74) *Attorney, Agent, or Firm*—Fliesler Meyer LLP

(57) ABSTRACT

This invention relates to methods for the treatment or prevention of central nervous system (CNS) cell damage and functional damage in mammals due to demyelinating disease including multiple sclerosis. More specifically, the invention comprises a method of treating a demyelinating disease of the CNS in a mammal, the method comprising co-administering to the mammal, either sequentially or simultaneously, GPE or analogues or peptidomimetics or a prodrug thereof, or a pharmaceutically acceptable salt thereof, and an AMPA (α-amino-3-hydroxy-5-methyl-4-isoxazolepropionate)/kainate antagonist, or a pharmaceutically acceptable salt thereof, and an anti-inflammatory agent.

49 Claims, 7 Drawing Sheets

Glutamate receptor-2

NMDAR1

TREATMENT OF DEMYELINATING DISEASES

RELATED APPLICATIONS

This application claims priority under 35 U.S.C. § 371 to PCT/US01/32198, having an International Filing Date of Oct. 11, 2001, which claimed priority to New Zealand Application Ser. No. 507,478, filed Oct. 12, 2000. Each of the above applications is herein incorporated fully by reference.

FIELD OF THE INVENTION

This invention relates to methods for the treatment or prevention of central nervous system (CNS) cell damage and functional damage in mammals due to demyelinating diseases including multiple sclerosis.

BACKGROUND OF THE INVENTION

Demyelinating conditions are a group of neurological disorders in which the lipid protein composite substance myelin surrounding axons of neurons which increases their ability to conduct electrical signals degenerates. This group of conditions includes acute and chronic encephalomyelitis, optic neuritis, transverse myelitis, Devic's disease, the leucodystrophies, multiple sclerosis, progressive multifocal leukoencephalopathy, central pontine myelinolysis, neuromyelitits optica, diffuse cerebral sclerosis of Schilder, acute and subacute necrotizing haemorrhagic encephalitis.

The most well-known of these conditions is multiple sclerosis which affects 350,000 Americans and is, with the exception of trauma, the most frequent cause of neurologic disability in early to middle adulthood. There are generally considered to be 3 forms of multiple sclerosis: relapsing, progressive, and inactive. The disease is characterized by selective demyelination of CNS axons, inflammation, and gliosis. The cause of multiple sclerosis is unknown but is thought to have an autoimmune etiology initiated by exposure to a virus in genetically predisposed individuals.

Multiple sclerosis derives its name from the multiple scarred areas visible on macroscopic examination of the brain. Areas of tissue affected in this manner are called plaques which range in size between 1 mm and several centimetres. Demyelinating lesions are historical evidence of the occurrence of or the continued presence of perivascular lesions. Occasionally, plaques are also present in gray matter. The multiple sclerosis lesion is defined as including both perivascular and demyelinating lesions. Demyelination, along with causing conduction abnormalities between neurons, can, in severe cases, lead to premature death.

Myelin is produced by specialized cells (generically referred to as glia). In the CNS, the main myelin-producing glia are named oligodendrocytes. Injury to myelin sheaths surrounding axons may interrupt communication between neurons and produce myelin breakdown. When myelin sheaths or oligodendrocytes sustain injury, entire segments of myelin degenerate, and their remnants are phagocytosed by macrophages, and to a much lesser degree, by astrocytes. This is called "primary demyelination" if most axons remain uninjured and is characteristic of the myelin breakdown seen in multiple sclerosis. In multiple sclerosis, and in experimental autoimmune encephalomyelitis (EAE), an animal model of multiple sclerosis, encephalitogenic leukocytes penetrate the blood brain barrier and damage the myelin sheath of nerve fibres (Raine, 1991, 1994; Martin and McFarland, 1995; Cannella and Raine, 1995; Brosnan and Raine, 1996).

The $\beta7$ integrin subfamily of cell adhesion molecules consists of two members, $\alpha4\beta7$ (Holzmann and Weissman, 1989; Yuan et al., 1992) and $\alpha E\beta7$ (Parker et al., 1992; Krissansen et al., 1992), whose expression is restricted to leukocytes. $\alpha4\beta7$ mediates the adherence of lymphocytes to high endothelial venules (HEV) via its preferred ligand mucosal addressin cell adhesion molecule-1 (MAdCAM-1, Berlin et al., 1993; Briskin et al., 1993; Yang et al., 1995), whereas $\alpha E\beta7$ mediates the adhesion of intraepithelial lymphocytes of the intestine to the intestinal epithelium via an interaction with E-cadherin (Karecla et al., 1995; Cepek et al., 1994, Berg et al., 1999).

In gene knockout mice deficient in the $\beta7$ integrin subfamily, the gut-associated lymphoid tissue (GALT) is severely impaired due to a failure of $\beta7-/-$lymphocytes to adhere to blood vessel walls at the site of transmigration into the GALT (Wagner et al., 1996). Further, in non-obese diabetic (NOD) mice, treatment with anti-$\beta7$ or anti-MAdCAM-1 mAbs provides protection against the spontaneous development of diabetes and insulitis, presumably by blocking lymphocyte migration into the inflamed pancreas (Yang et al., 1997). These examples demonstrate that $\alpha4\beta7$-MAdCAM-1 interactions play critical roles in allowing the entry of leukocytes into chronically inflamed tissues.

A role for $\alpha4$ integrins in the establishment of EAE was demonstrated by in vivo administration of anti-$\alpha4$ integrin antibodies which diminished the paralysis associated with EAE (Yednock et al., 1992; Baron et al., 1993). Further, the suppressive effects of TNFbp on the development of EAE appears to correlate with down-regulation of VCAM-1/$\alpha4\beta1$ (Selmaj et al., 1998). A humanized anti-integrin $\alpha4$ subunit antibody prevented the development of new lesions in a recent clinical trial (Tubridy et al., 1999). Hence $\alpha4$-integrins play a crucial role in mediating the pathogenesis of demyelinating disease of the CNS.

An antibody directed against the integrin $\beta7$ subunit, the partner chain for the $\alpha4$ subunit, greatly attenuates a non-remitting form of EAE, induced by adoptive transfer of myelin oliogodendrocyte peptide (MOG35-55)-stimulated T cells (Kanwar et al., 2000a). Combinational treatment with both anti-$\beta7$ and $\alpha4$ integrin subunit antibodies lead to more rapid and complete remission than that obtained with anti-$\alpha4$ antibody alone, potentially implicating a role for $\alpha E\beta7$ in disease progression. Remission correlated with the down-regulation of the vascular addressins VCAM-1, MAdCAM-1, and ICAM-1 on cerebral blood vessels. Attenuated forms of disease were induced by adoptive transfer of either wild-type encephalitogenic T cells to $\beta7$-deficient gene knockout mice, or of $\beta7-/-$encephalitogenic T cells to wild-type recipients. The former indicates that $\beta7^{+ve}$ recruited cells contribute to disease progression. Thus $\alpha4\beta1$, $\alpha4\beta7$, and $\alpha E\beta7$ integrins may all play a contributory role in the progression of chronic forms of demyelinating disease, and together with their ligands could be potential targets for improved treatment of some forms of multiple sclerosis.

MAdCAM-1, the preferential ligand for $\alpha4\beta7$, is predominantly expressed on specialized HEV formed at chronically inflamed sites (Streeter et al., 1988), and is particularly noticeable on HEV-like endothelia in relapsing brain lesions of mice with EAE (Cannella et al., 1991). An antibody directed against MAdCAM-1 prevented the development of a progressive, non-remitting form of EAE, actively induced by injection of myelin oligodendrocyte peptide (MOG35-55)

autoantigen (Kanwar et al., 2000b). Combinational treatment with both anti-MAdCAM-1, VCAM-1, and ICAM-1 (ligand for integrin LFA-1) mAbs led to more rapid remission than that obtained with anti-MAdCAM-1 antibody alone. However, neither MAdCAM-1 monotherapy, nor combinational antibody blockade was preventative when administered late in the course of disease progression. Nevertheless, MAdCAM-1 plays a major contributory role in the progression of chronic EAE, and is a potential therapeutic target for the treatment of MS. Anti-vascular addressin therapy must be given early in the course of disease prior to the establishment of irreversible damage if it is to be effective as a single treatment modality.

Integrin-mediated entry of leukocytes into the CNS leads to markedly elevated concentrations of glutamate, a major excitatory amino acid neurotransmitter, in the cerebrospinal fluid of patients suffering from multiple sclerosis (Stover et al., 1997). Glutamate receptors of the AMPA/kainate class are expressed on oligodendrocytes. Low concentrations of glutamate, AMPA, or kainate kill oligodendrocytes in vitro, indicating that glutamate injures oligodendrocytes thereby reducing myelination during EAE (McDonald et al., 1998).

The AMPA/kainate receptor antagonist 2,3-dihydroxy-6-nitro-7-sulfamoylbenzo(f)quinoxaline (NBQX) inhibits the excitotoxic effects of glutamate on oligodendrocytes, and slightly ameliorates the pathogenesis of EAE (Smith et al., 2000; Pitt et al., 2000).

GPE is a tripeptide consisting of amino acids Gly-Pro-Glu. It and its di-peptide derivatives Gly-Pro and Pro-Glu were first disclosed by Sara et al in EP 0366638. The suggestion made by Sara et al is that GPE has neuromodulatory properties (able to affect the electrical properties of neurons).

GPE has also been established as having neuroprotective properties and therefore has utility in the prevention or inhibition of neuronal and glial cell death (WO 95/17204, AU 700838).

GPE has also been established as being able to upregulate neural enzymes and therefore has utility in increasing the effective amount of choline acetyl transferase (ChAT), nitric oxide synthetase (NOS), glutamic acid decarboxylase (GAD) (WO 98/14202) and tyrosine hydroxylase (WO 99/65509) in the brain.

GPE has also been established as having cross-receptor activity in that it inhibits glutamate binding to the N-methyl-D-aspartate (NMDA) receptor (U.S. Pat. No. 5,804,550) and prevents neuronal death in the hippocampus injured by NMDA (Saura et al., 1999).

Current drug management of multiple sclerosis consists of immunosuppression to arrest the disease process and for arresting the symptoms. No drugs are currently successful in intervening in the disease process.

One approach that has been tried has been to administer neuroprotective agents to repair the damage to the CNS, such as the kainate antagonist NBQX as described in Smith et al., 2000 and Pitt et al., 2000. This research demonstrated that administration of NBQX at the early stages of disease in an animal model of the multiple sclerosis could attenuate but not block the disease process.

It is an object of the present invention to provide a method of treating demyelinating diseases which goes some way towards overcoming the disadvantages of the prior art, and in particular which is useful in treating such diseases when in an advanced state, or at least to provide the public with a useful choice.

It is a further object of the invention to provide a method for treating or preventing plaque formation and the demyelination of axons so that the affected areas of the CNS are protected from damage resulting from demyelinating disease including multiple sclerosis.

STATEMENT OF THE INVENTION

Accordingly, in a broad aspect the invention comprises a method of treating a demyelinating disease of the CNS in a mammal, the method comprising co-administering to the mammal, either sequentially or simultaneously, GPE or analogues or peptidomimetics or a prodrug thereof, or a pharmaceutically acceptable salt thereof, and an AMPA ($\alpha$-amino-3-hydroxy-5-methyl-4-isoxazolepropionate)/kainate antagonist or a pharmaceutically acceptable salt thereof.

Preferably, the mammal is a human.

Preferably, the demyelinating disease is in an early state.

Most preferably, the demyelinating disease is in an advanced state.

Preferably, the demyelinating disease is multiple sclerosis.

Preferably, the AMPA/kainate antagonist is NBQX.

Preferably, the anti-inflammatory agent is an agent which inhibits the function of a cell adhesion molecule.

Most preferably, the anti-inflammatory agent is an antibody directed against the addressin MAdCAM-1 and/or its integrin $\alpha 4$ receptors ($\alpha 4\beta 1$ and $\alpha 4\beta 7$).

In a further aspect, the present invention provides the use of GPE and analogues and peptidomimetics or a prodrug thereof in the preparation of a medicament for co-administration with an AMPA/kainate antagonist and an anti-inflammatory agent to treat a demyelinating disease of the CNS.

In a further aspect, the present invention provides the use of an AMPA/kainate antagonist and an anti-inflammatory agent, which preferably inhibits the function of a cell adhesion molecule, in the preparation of a medicament for sequential or simultaneous administration with GPE and analogues and peptidomimetics or a prodrug thereof to treat a demyelinating disease of the CNS.

In a further aspect, the present invention provides the use of an anti-inflammatory agent in the manufacture of a medicament for sequential or simultaneous co-administration with GPE and analogues and peptidomimetics or a prodrug thereof and an AMPA/kainate antagonist to treat a demyelinating disease of the CNS.

Preferably, the anti-inflammatory agent inhibits the function of a cell adhesion molecule, and more preferably is an antibody directed against addressin MAdCAM-1 and/or its integrin $\alpha 4$ receptors ($\alpha 4\beta 1$ and $\alpha 4\beta 7$).

It will be usual for the dosage range of GPE administered to be from about 1 µg to about 100 mg of GPE per kg of body weight of the mammal.

It will be usual for the dosage range of NBQX administered to be from about 60 µg to about 600 mg of NBQX per kg of body weight of the mammal.

It will be usual for the dosage range of anti MAdCAM-1 antibody administered to be from about 30 µg to about 300 mg of anti MAdCAM-1 antibody per kg of body weight of the mammal.

In still a further aspect, the present invention comprises a therapeutic kit for the treatment of a demyelinating disease of the CNS, the kit comprising GPE and analogues and peptidomimetics or a prodrug thereof and an AMPA/kainate antagonist and an anti-inflammatory agent.

Although the present invention is defined broadly above, it will be appreciated by those skilled in the art that it is not limited thereto but includes embodiments of which the following description provides examples.

DESCRIPTION OF THE DRAWINGS

The invention will now be described in more detail with reference to the accompanying drawings, in which.

DESCRIPTION OF THE INVENTION

Figure 1:
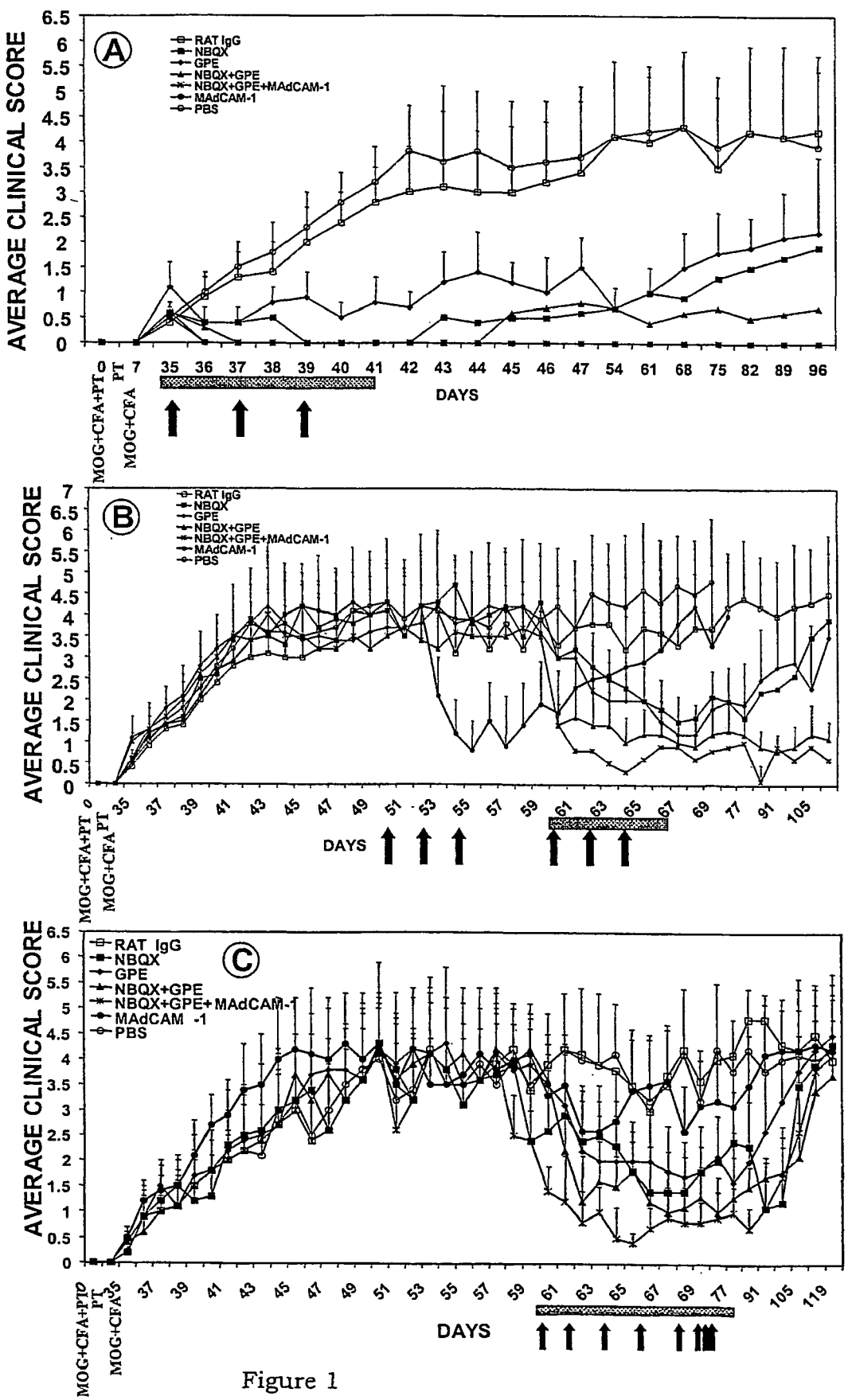
FIG. 1 shows that the combination of the neuroprotectors GPE and NBQX causes sustained remission of advanced EAE, which is further enhanced by anti-MAdCAM-1 antibody blockade. (A) Neuroprotectors and cell adhesion blockade with an anti-MAdCAM-1 antibody attenuate the early development of EAE. EAE was actively induced by administration of MOG35-55 peptide and pertussis toxin, leading to peak disease 35 days later. Anti-MAdCAM-1 mAb MECA-367 (500 µg in PBS) was administered thrice on alternate days 35, 37, and 39, whereas neuroprotectors (30 µg GPE in PBS; 6 mg NBQX in PBS) were given daily for 6 days (days 35 to 39), where 50% of reagent was given ip and 50% iv. (B) Combination of GPE and NBQX caused sustained remission of advanced EAE, which is further enhanced by anti-MAdCAM-1 antibody blockade. EAE was induced as above. Anti-MAdCAM-1 mAb MECA-367 (500 µg) was administered thrice on alternate days 51, 53, and 55, or 60, 62, and 64; whereas neuroprotectors (30 µg GPE; and 6 mg NBQX) were given daily for 7 days (days 60 to 66), where 50% of reagent was given intraperitoneally (ip) and 50% intravenously (iv). EAE was induced as above. (C) Prolonged combination therapy is non-toxic, and provides sustained protection. EAE was induced as above. Anti-MAdCAM-1 mAb MECA-367 (500 µg) was administered eight times on alternate days 60 to 74; whereas neuroprotectors (30 µg GPE; and 6 mg NBQX) were given daily for 18 days (days 60 to 78), where 50% of reagent was given ip and 50% iv. Arrows refer to antibody administration, whereas the speckled line refers to neuroprotector administration.

As defined above, the invention provides a method for treating demyelinating diseases of the CNS, that has particular application in treating the diseases at an advanced stage.

The present invention resides in the applicant's surprising finding that the effectiveness of the synergistic combination of GPE and the AMPA/kainate antagonist NBQX agents can be enhanced by administration of an anti-inflammatory agent, such that the effectiveness of the neuroprotective agents and the anti-inflammatory agent in combination exceeds that of either the two neuroprotective agents or the anti-inflammatory agent when administered alone.

The therapeutic methods of the invention therefore comprise administering GPE and an AMPA/kainate antagonist and an anti-inflammatory agent, preferably an anti-inflammatory agent which inhibits the activity of a cell adhesion molecule and most preferably the anti-inflammatory agent is an antibody directed against the cell adhesion molecule MAdCAM-1 and/or its integrin α4 receptors (α4β1 and (α4β7), to a patient suffering from a demyelinating disease of the CNS. The methods of the invention may be used to treat inflammatory diseases including autoimmune diseases including multiple sclerosis, as well as viral and bacterial induced encephalitis, and have particular application in treating advanced forms of the diseases.

The compound NBQX is preferred as the AMPA/kainate antagonist for use in the methods of the present invention.

Other anti-inflammatory agents that may be used in the methods of the present invention include anti-integrin alpha 4 subunit reagents, anti-integrin beta 7 subunit reagents, anti-integrin beta 2 subunit reagents, anti-integrin alpha L subunit reagents, anti-VCAM-1 reagents and anti-ICAM-1 reagents.

Pharmacology and Utility

GPE and NBQX are anti-apoptotic and anti-necrotic. Their anti-apoptotic and anti-necrotic activity in vivo can be measured by cell counts, by methods such as those discussed in Klempt et al., 1992. Their activity can also be measured in vitro.

The therapeutic ratio of a compound can be determined, for example, by comparing the dose that gives effective anti-apoptotic and anti-necrotic activity in a suitable in vivo model such as experimental immune encephalomyelitis [Mendel et al., 1995] in a suitable animal species such as the mouse, with the dose that gives significant weight change (or other observable side-effects) in the test animal species.

Pharmaceutical Compositions and Administration

In general, compounds of this invention will be administered in therapeutically effective amounts by any of the usual modes known in the art, either singly or in combination with at least one other compound of this invention and/or at least one other conventional therapeutic agent for the disease being treated. A therapeutically effective amount may vary widely depending on the disease or injury, its severity, the age and relative health of the patient being treated, the potency of the compound(s), and other factors. As an anti-apoptotic and anti-necrotic agent, therapeutically effective amounts of GPE in this invention may range from 1 μg to 100 mg per kilogram (mg/Kg) mass of the animal, for example, 0.1 to 10 mg/Kg, with lower doses such as 0.001 to 0.1 mg/Kg, eg. about 0.01 mg/Kg, being appropriate for administration through the cerebrospinal fluid, such as by intracerebroventricular administration, and higher doses such as 1 to 100 mg/Kg, e.g. about 10 mg/Kg, being appropriate for administration by methods such as oral, systemic (eg. transdermal), or parenteral (eg. intravenous) administration. A person of ordinary skill in the art will be able without undue experimentation, having regard to that skill and this disclosure, to determine a therapeutically effective amount of a compound of this invention for a given disease or injury.

The term "insult" signifies injury, irritation, or trauma.

As an anti-apoptotic and anti-necrotic agent, therapeutically effective amounts of NBQX in this invention may range from 60 μg to 600 mg per kilogram (mg/Kg) mass of the animal, for example, 0.6 to 60 mg/Kg, with lower doses such as 0.006 to 0.6 mg/Kg, e.g. about 0.06 mg/Kg, being appropriate for administration through the cerebrospinal fluid, such as by intracerebroventricular administration, and higher doses such as 6 to 600 mg/Kg, e.g. about 60 mg/Kg, being appropriate for administration by methods such as oral, systemic (e.g. transdermal), or parenteral (e.g. intravenous) administration. A person of ordinary skill in the art will be able without undue experimentation, having regard to that skill and this disclosure, to determine a therapeutically effective amount of a compound of this invention for a given disease or injury.

As an anti-inflammatory agent, therapeutically effective amounts of anti-MAdCAM-1 antibody in this invention may range from 30 μg to 300 mg per kilogram (mg/Kg) mass of the animal, for example, 0.3 to 30 mg/Kg, with lower doses such as 0.003 to 0.3 mg/Kg, e.g. about 0.03 mg/Kg, being appropriate for administration through the cerebrospinal fluid, such as by intracerebroventricular administration, and higher doses such as 3 to 300 mg/Kg, e.g. about 30 mg/Kg, being appropriate for administration by methods such as oral, systemic (eg. transdermal), or parenteral (e.g. intravenous) administration. A person of ordinary skill in the art will be able without undue experimentation, having regard to that skill and this disclosure, to determine a therapeutically effective amount of a compound of this invention for a given disease or injury.

In general, compounds of this invention will be administered as pharmaceutical compositions by one of the following routes: oral, topical, systemic (eg. transdermal, intranasal, or by suppository), parenteral (eg. intramuscular, subcutaneous, or intravenous injection), by administration to the CNS (eg. by intraspinal or intracisternal injection); by implantation, and by infusion through such devices as osmotic pumps, transdermal patches, and the like. Compositions may take the form of tablets, pills, capsules, semi-solids, powders, sustained release formulation, solutions, suspensions, elixirs, aerosols, or any other appropriate compositions; and comprise at least one compound of this invention in combination with at least one pharmaceutically acceptable excipient. Suitable excipients are well known to persons of ordinary skill in the art, and they, and the methods of formulating the compositions, may be found in such standard references as Gennaro AR: Remington: The Science and Practice of Pharmacy, 20$^{th}$ ed., Lippincott, Williams & Wilkins, 2000. Suitable liquid carriers, especially for injectable solutions, include water, aqueous saline solution, aqueous dextrose solution, and the like, with isotonic solutions being preferred for intravenous, intraspinal, and intracisternal administration and vehicles such as artificial cerebrospinal fluid being also especially suitable for administration of the compound to the CNS.

Compounds of this invention are also suitably administered by a sustained-release system. Suitable examples of sustained-release compositions include semi-permeable polymer matrices in the form of shaped articles, e.g., films, or microcapsules. Sustained-release matrices include polylactides (U.S. Pat. No. 3,773,919; EP 58,481), copolymers of L-glutamic acid and gamma-ethyl-L-glutamate (Sidman et al., 1983), poly(2-hydroxyethyl methacrylate) (Langer et al., 1981), ethylene vinyl acetate (Langer et al., supra), or poly-D-(–)-3-hydroxybutyric acid (EP 133,988). Sustained-release compositions also include a liposomally entrapped compound. Liposomes containing the compound are prepared by methods known per se: DE 3,218,121; Hwang et al., 1980; EP 52,322; EP 36,676; EP 88,046; EP 143,949; EP 142,641; Japanese Pat. Appln. 83-118008; U.S. Pat. Nos. 4,485,045 and 4,544,545; and EP 102,324. Ordinarily, the liposomes are of the small (from or about 200 to 800 Angstroms) unilamellar type in which the lipid content is greater than about 30 mole percent cholesterol, the selected proportion being adjusted for the most efficacious therapy.

Compounds of this invention may also be PEGylated to increase their lifetime in vivo, based on, e.g., the conjugate technology described in WO 95/32003.

Desirably, if possible, when administered as anti-apoptotic and anti-necrotic agents, GPE and NBQX and an anti-MAdCAM antibody, as an anti-inflammatory agent, will be administered orally. The amount of a compound of this invention in the composition may vary widely depending on the type of composition, size of a unit dosage, kind of excipients, and other factors well known to those of ordinary skill in the art. In general, the final composition may comprise from 0.0001 percent by weight (% w) to 10% w of the compound of this invention, preferably 0.001% w to 1% w, with the remainder being the excipient or excipients.

The invention will now be described in more detail with reference to the following non-limiting examples.

EXAMPLES

Experiments

The following experimental protocol followed guidelines approved by the University of Auckland Animal Ethics Committee.

Animal Model of MS

C57Bl/6 mice (8–10 week old) were injected subcutaneously in one flank with 300 μg of MOG35-55 peptide (MEVGWYRSPFSRVVHLYRNGK: SEQ ID NO:1) synthesized by Mimotapes Pty Ltd, Clayton, Australia and emulsified in CFA containing 500 μg of Mycobacterium tuberculosis H37Ra (DIFCO Laboratories, Detrit, USA). They also received 500 ng of pertussis toxin (List Biological Laboratories, CA, USA) in 200 μl PBS intravenously via the tail vein, followed 48 hours later by a second dose. A second injection of MOG peptide was given in the absence of pertussis toxin one week later in the opposite flank, as described previously (Kanwar et al., 2000b).

Treatment Protocols

Two treatment protocols were employed, involving the treatment of early disease, versus advanced disease. For early disease, reagents were administered at day 35 (following MOG injection). Antibody was administered thrice on alternate days, whereas neuroprotectors were given daily for 6 days, where 50% of reagent was given ip and 50% iv. In the treatment of advanced disease, therapy as above was initiated at day 60, with either three or eight anti-MAdCAM-1 mAb injections, and neuroprotectors given daily for either 7 or 18 days.

Clinical Scoring and Disability Scales

The mice were monitored daily and scored according to the following scale: 0, no clinical signs of EAE; 1, limp tail; 2, partial hind limb paralysis; 3, complete hind limb paralysis; 4, complete hind limb and partial fore limb paralysis; 5, paralysis extending to diaphragm; 6, hind and fore limb paralysis; 7, death due to EAE. Paralysis extending to the diaphragm was denoted as difficulty in remaining upright. They had to be maintained in a state of hind-limb paralysis, hence care was shown in the provision of drinking water, food, and comfort. The daily mean clinical score for each group is the mean disease score of at least five mice. The body weight of animals was measured regularly throughout the experiments. The expanded disability status scale for EAE treated mice was scored using an earlier published scoring system (Villoslada et al. 2000).

Antibodies, Antibody Blocking and Histochemistry

The rat hybridoma MECA-367 (rat IgG2a),5 which secretes a mAb against mouse MAdCAM-1 was either provided by Dr Eugene Butcher, Stanford University, Stanford, Calif. (FIGS. 1A and B), or obtained directly from the American Type Culture Collection, Rockville, Md. (FIG. 1C, and remainder of studies). Rat IgG obtained from Sigma Co., USA, served as a control. Antibodies were administered into the tail vein (70% of mAb) and intraperitoneally (30% of mAb) at 10 mg/Kg separately or in combination on alternate days at the time points indicated (FIGS. 1–4). The rat IgG control antibody was also administered at 10 mg/Kg. Backbones from sacrificed mice were frozen in isopentane at −70° C. Transverse 10 μm sections made through the spinal cord of control and diseased mice, in each case made at the same levels of the cord, were mounted on poly L-lysine-coated slides, and stained with haematoxylin and eosin.

An antibody to exon-2 of MBP was raised in a rabbit by coupling a mouse MBP exon 2 peptide (H-DSHTRT-THYGSLPQKSQHGRTQDENPVVHFFKNCG-OH: SEQ ID NO:2) to the carrier protein thyroglobulin. Rabbits were immunized four times with 0.5 to 1 mg of peptide at 2 to 4 week intervals. The antibody titre was determined at 1:8000 by ELISA. The antibody was used to stain the spinal cord sections at 1:50 dilution.

Neuropathology

Mice were perfused through the left cardiac ventricle with ice-cold PBS or glutaraldehyde, and the CNS including brain and spinal cord were prepared for frozen or epoxy sections, respectively. Thin slices were taken at all levels of the CNS including spinal cord (cervical, midthoracic, T11, T12/13, upper lumbar, L6, L7 and sacral) and sacral roots. One-μm thick epoxy sections taken from different levels of the spinal cord were stained with toluidine blue, and examined by light microscopy by an investigator blinded to the sample identity. Multiple sections from the spinal cord were scored from 0 to 5 for inflammation, demyelination, remyelination, and axonal necrosis or damage, using a previously published scoring system (Moore et al., 2000).

Frozen sections from lumbar spinal cord (10 μm) were acetone-fixed and immunostained for oligodendrocyte content with an antibody against CNPase (Sigma; diluted 1:100); for axonal damage with an antibody against non-phosphorylated neurofilament-H (SM 1-32; Stemberger Monoclonals Incorporated, Lutherville, Md., USA; diluted 1:1000), and for GluR2 and NR1 content using mouse mAbs obtained from Zymed Laboratories Inc., Carlton, San Francisco, Calif. Antibody staining was visualized with an avidin:biotinylated enzyme complex (Vector Laboratories, Burlingame, Calif., USA). Sections were viewed under a light microscope, and cells stained with the anti-CNPase and SM 1-32 antibodies were counted.

Western Blot Analysis

PBS-perfused spinal cords were homogenized in lysis buffer (50 mM Tris pH 7.4, 100 μM EDTA, 0.25 M sucrose, 1% sodium dodecyl sulfate [SDS], 1% Nonidet P-40 [NP40], 1 μg/mL leupeptin, 1 μg/mL pepstatin A, and 100 μM phenylmethylsulfonylfluoride) at 4° C. using a motor-driven homogenizer (Virtus, Gardiner, N.Y.). Spinal cord lysates from each group of mice were pooled and centrifuged at 10000 g for 10 minutes at 4° C. to remove tissue debris. Protein concentrations of the supernatants were determined as described (Peterson, 1983), and 100 μg of protein resolved on 10% polyacrylamide SDS-gels under reducing conditions and then electrophoretically transferred to Hybond C Extra nitrocellulose membranes (Amersham Life Science, England). The membranes were blocked with 3% bovine serum albumin in TBS-T (20 mM Tris, 137 mM NaCl, pH 7.6 containing 0.1% Tween-20) for 2 hours at room temperature. Immunodetection was accomplished by incubation overnight at 4° C. with SM1-32 (1:500 dilution), anti-CNPase (1:100 dilution) antibody, or anti-GluR2 and NR1 mAbs (1:200 dilution). The membranes were washed thrice with TBS-T and incubated with horseradish peroxidase-conjugated anti-mouse IgG (Sigma) diluted 1:5000 in TBS-T. Immunoreactivity was detected by Enhanced Chemiluminescence (Amersham International plc. England) and autoradiography.

In Situ Detection of Apoptotic Cells by the TUNEL Assay

Cells undergoing apoptosis were identified using the in situ TUNEL assay. Five-µm thick serial sections of brain and spinal cord were prepared to detect apoptosis by TUNEL (i.e., terminal deoxynucleotidyl transferase-mediated deoxyuridine triphosphate-digoxigenin nick end labeling) staining using the In Situ Apoptosis Detection Kit from Boehringer Mannheim (Germany). Briefly, frozen sections were fixed in 4% paraformaldehyde, permeabilized in 0.1% Triton X-100, incubated with 20 µL TUNEL reagent for 60 minutes at 37° C., and then examined by fluorescence microscopy. Adjacent sections were counterstained with hematoxylin and mounted onto poly-L-lysine coated slides to allow the total number of nucleated cells to be counted. The percentage of apoptotic cells was assessed in ten randomly selected fields viewed at 40× magnification. The apoptotic index (AI) was calculated as follows: AI=number of apoptotic (TUNEL-positive) cells×100/total number of nucleated cells.

Results

Suppression of the Development of EAE by Early Blockade of Inflammation, and Excitotoxic Damage, or Addition of Neuroprotector GPE The first signs of clinical EAE ensued between days 28 to 35, depending on the particular batch of $MOG_{35-55}$ peptide autoantigen, leading to chronic sustained paralysis of the hind limbs eight days later (FIG. 1). The prolonged persistence of clinical symptoms at the same level for several months is characteristic of MOG-induced EAE in the C57BL/6 strain of mice (Mendel et al., 1995). Three iv and ip injections of anti-MAdCAM-1 mAb, given on days 35, 36, and 37 following injection of autoantigen completely prevented the induction of EAE such that no overt clinical symptoms could be observed for 60 days after suspension of antibody treatment (FIG. 1A).

GPE given daily from day 35 for 6 days suppressed EAE, up to 27 days after suspension of treatment (disease score 0.4 to 2.2 compared to 2.6 to 5.9 for controls). However, thereafter disease severity gradually increased. NBQX given daily for 6 days also suppressed EAE, but to a greater extent than achieved with GPE, however as with GPE the severity of disease gradually increased 27 days following suspension of treatment. In contrast, combined treatment with GPE and NBQX led to sustained suppression of disease symptoms, at least for the 55 days the animals were monitored following suspension of treatment. The triple combination of anti-MAdCAM-1 mAb, NBQX and GPE, as with anti-MAdCAM-1 mAb alone completely prevented the development of disease in all mice.

Combination Treatments are Effective in the Treatment of Advanced EAE

As described previously, anti-CAM therapy to block inflammation is only preventative when administered early, prior to establishment of significant nerve damage. Thus, three injections of anti-MAdCAM-1 mAb at high dose starting on day 51 caused initial remission of disease, but this was quickly followed by a gradual and complete relapse after suspension of treatment (FIG. 1B). NBQX and GPE administered for 7 days as monotherapies only caused temporary remission, and by day 105 the disease had almost returned to control levels of crippling paralysis. In contrast, the combination of NBQX with GPE appeared to be synergistic as the disease was suppressed (disease score reduced from 4.5 to 1) for 40 days following suspension of treatment (FIG. 1B). This indicates that administering a combination of GPE and NBQX delays disease progression. It makes no sense to inhibit demyelinating inflammation without attempting repair of the CNS; or achieving repair without damage limitation.

For the first time we have combined both approaches to successfully treat advanced disease. Remarkably, simultaneous administration of anti-MAdCAM-1 mAb, NBQX and GPE delivered sustained protection (disease score reduced from 5 to <1) against disease progression.

Long-term treatment is non-toxic, but has to be maintained to be protective. The various treatment regimes were administered for 16 days in order to determine whether prolonged treatment was non-toxic (FIG. 1C). In this experiment, similar results were obtained as in FIG. 1B. Thus the effectiveness of the treatments was in the order NBQX+GPE+anti-MAdCAM-1>NBQX+GPE>NBQX>GPE; whereas anti-MAdCAM-1 monotherapy only weakly attenuated disease severity. However, the disease relapsed in all cases following suspension of treatment, suggesting that therapy must be maintained if it is to be consistently effective.

Two mice died for unknown reasons in the NBQX+GPE combination, but not in the NBQX+GPE+anti-MAdCAM-1 combination. Since no mice from the triple combination, or the earlier experiment (FIG. 1B) had died, the combinational treatment protocols appear to be safe and effective at the doses employed.

Figure 2:
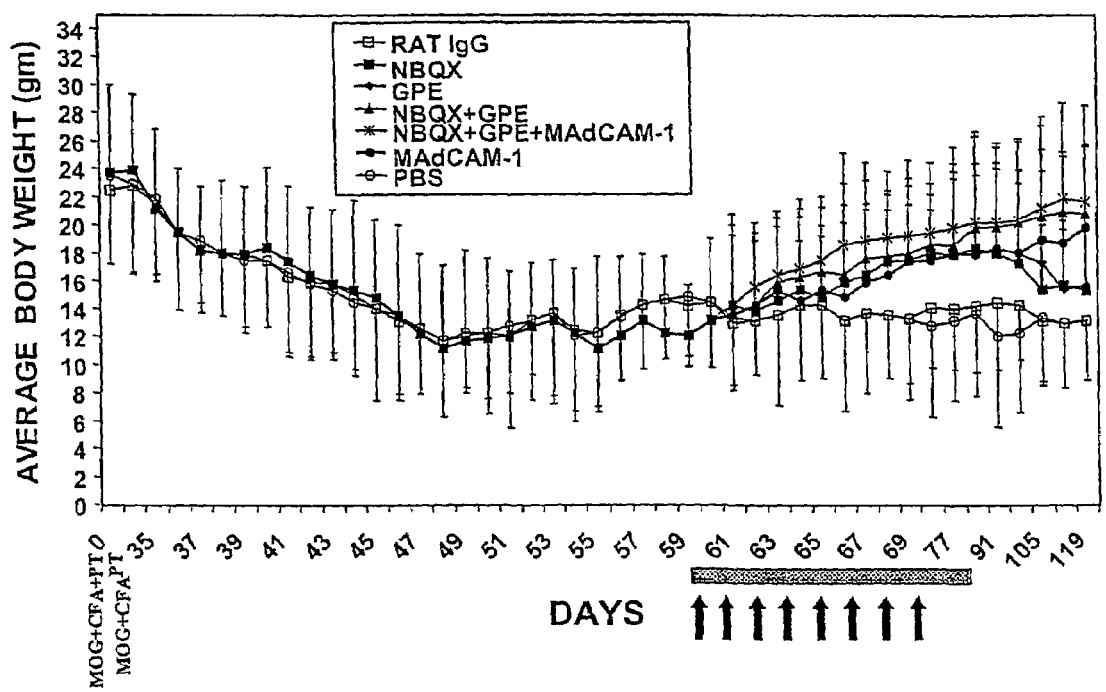
FIG. 2 shows the changes in average body weight associated with disease progression and remission following therapy. The average body weight of mice was monitored after disease onset, and following treatment. Arrows refer to antibody administration, whereas the speckled line refers to neuroprotector administration.

Weight loss was found to correlate with disease severity. At disease onset the body weight of mice rapidly decreased, such that mice had lost 50% of their average body weight within 2 weeks of disease progression (FIG. 2). Mice experienced a weight gain following treatment that correlated with the efficacy of the particular treatment regime (ie NBQX+GPE+anti-MAdCAM-1>NBQX+GPE>NBQX, GPE, or MAdCAM-1 monotherapies), where the weight of mice receiving the triple treatment returned almost to normal.

The disability scores (Table 1) for the various treatment groups correlated well with the clinical scores of paralysis. Diseased mice displayed discernible impairments in spontaneous mobility, tone, motor function (grip), sensory function, and shiny hair/skin firmness. The total clinical scores inversely correlated with the efficacy of the particular treatment regime (ie NBQX+GPE+anti-MAdCAM-1>NBQX+GPE>NBQX or GPE or anti-MAdCAM-1 mAb). For example the total scores at day 70 were 3 for NBQX+GPE+anti-MAdCAM-1, 10 for NBQX+GPE, 10 for GPE, 30 for NBQX, 19 anti-MAdCAM-1 mAb, compared to 35 for rat IgG treated control mice).

TABLE 1

Disability status scale.

| | Maximal disability score days after immunization (mean values) | | | | | | | | | | | | | | | | | |
|---|---|---|---|---|---|---|---|---|---|---|---|---|---|---|---|---|---|---|
| | Rat IgG' | | | | | | GPE | | | | | | NBQX | | | | | |
| Disability function | 55 | 60 | 65 | 70 | 75 | 119 | 55 | 60 | 65 | 70 | 75 | 119 | 55 | 60 | 65 | 70 | 75 | 119 |
| 1. Alertness | 2 | 2 | 1 | 1 | 2 | 1 | 2 | 2 | 1 | 1 | 1 | 1 | 2 | 2 | 1 | 1 | 1 | 1 |
| 2. Spontaneous mobility | 3 | 3 | 2 | 3 | 2 | 2 | 3 | 3 | 2 | 3 | 3 | 2 | 3 | 3 | 2 | 3 | 3 | 2 |
| 3. Tremor | 2 | 2 | 2 | 2 | 2 | 2 | 2 | 2 | 0 | 0 | 0 | 1 | 2 | 2 | 0 | 0 | 0 | 1 |
| 4. Tone* | 12 | 12 | 12 | 12 | 8 | 8 | 12 | 12 | 8 | 4 | 4 | 4 | 12 | 12 | 8 | 4 | 4 | 4 |
| 5. Motor (grip)* | 12 | 12 | 12 | 12 | 8 | 12 | 12 | 12 | 4 | 4 | 0 | 0 | 12 | 12 | 4 | 4 | 8 | 4 |
| 6. Sensory* | | | | | | | | | | | | | | | | | | |
| Light touch | 8 | 8 | 4 | 8 | 4 | 4 | 8 | 8 | 0 | 0 | 0 | 4 | 8 | 8 | 0 | 0 | 4 | 4 |
| Pain | 8 | 8 | 4 | 8 | 4 | 8 | 8 | 8 | 0 | 0 | 0 | 4 | 8 | 8 | 0 | 0 | 8 | 4 |
| 7. Eye movements | 1 | 1 | 1 | 1 | 0 | 1 | 1 | 1 | 0 | 1 | 0 | 1 | 1 | 1 | 0 | 1 | 0 | 1 |
| 8. Vision (including pupillary reflex) | 1 | 1 | 1 | 1 | 1 | 1 | 1 | 1 | 0 | 0 | 1 | 0 | 1 | 1 | 0 | 0 | 1 | 0 |
| 9. Bladder function | 0 | 1 | 1 | 0 | 1 | 0 | 0 | 1 | 0 | 0 | 1 | 0 | 0 | 1 | 0 | 0 | 1 | 0 |
| 10. Other signs (shine hairs and loose skin) | 2 | 3 | 3 | 3 | 3 | 3 | 3 | 2 | 0 | 0 | 0 | 0 | 3 | 2 | 0 | 0 | 0 | 2 |
| Total expanded disability scale | 51 | 53 | 43 | 51 | 35 | 42 | 52 | 52 | 15 | 13 | 10 | 17 | 53 | 53 | 15 | 13 | 30 | 23 |

| | Maximal disability score days after immunization (mean values) | | | | | | | | | | | | | | | | | |
|---|---|---|---|---|---|---|---|---|---|---|---|---|---|---|---|---|---|---|
| | GPE + NBQX | | | | | | MAdCAM-1 | | | | | | GPE + NBQX + MAdCAM-1 | | | | | |
| Disability function | 55 | 60 | 65 | 70 | 75 | 119 | 55 | 60 | 65 | 70 | 75 | 119 | 55 | 60 | 65 | 70 | 75 | 119 |
| 1. Alertness | 2 | 2 | 1 | 1 | 1 | 1 | 2 | 2 | 1 | 1 | 1 | 1 | 2 | 2 | 0 | 0 | 1 | 1 |
| 2. Spontaneous mobiity | 3 | 3 | 2 | 3 | 3 | 2 | 3 | 3 | 2 | 1 | 0 | 2 | 3 | 3 | 0 | 0 | 1 | 1 |
| 3. Tremor | 2 | 2 | 0 | 0 | 0 | 1 | 2 | 2 | 0 | 0 | 0 | 1 | 2 | 2 | 0 | 0 | 0 | 1 |
| 4. Tone* | 12 | 12 | 8 | 4 | 4 | 4 | 12 | 12 | 8 | 0 | 4 | 4 | 8 | 12 | 0 | 0 | 0 | 0 |
| 5. Motor (grip)* | 12 | 12 | 4 | 4 | 0 | 0 | 12 | 12 | 4 | 4 | 4 | 4 | 12 | 12 | 0 | 4 | 0 | 0 |
| 6. Sensory* | | | | | | | | | | | | | | | | | | |
| Light touch | 8 | 8 | 0 | 0 | 0 | 4 | 8 | 8 | 0 | 0 | 4 | 4 | 8 | 8 | 0 | 0 | 0 | 4 |
| Pain | 8 | 8 | 0 | 0 | 0 | 4 | 8 | 8 | 0 | 0 | 4 | 4 | 8 | 8 | 0 | 0 | 0 | 4 |
| 7. Eye movements | 1 | 1 | 0 | 1 | 0 | 1 | 1 | 1 | 0 | 1 | 0 | 1 | 1 | 1 | 0 | 1 | 0 | 1 |
| 8. Vision (including pupillary reflex) | 1 | 1 | 0 | 0 | 1 | 0 | 1 | 1 | 0 | 0 | 1 | 0 | 1 | 1 | 0 | 0 | 1 | 0 |
| 9. Bladder function | 0 | 1 | 0 | 0 | 1 | 0 | 0 | 1 | 0 | 0 | 1 | 0 | 0 | 1 | 0 | 0 | 0 | 0 |
| 10. Other signs (shine hairs and loose skin) | 3 | 2 | 0 | 0 | 0 | 0 | 3 | 2 | 0 | 0 | 0 | 2 | 3 | 2 | 0 | 0 | 0 | 0 |
| Total expanded disability scale | 52 | 52 | 15 | 13 | 10 | 17 | 52 | 52 | 15 | 7 | 19 | 23 | 48 | 52 | 0 | 5 | 3 | 12 |

Neuropathological Evaluation Confirms Relative Efficacies of Treatment Regimes

Figure 3:
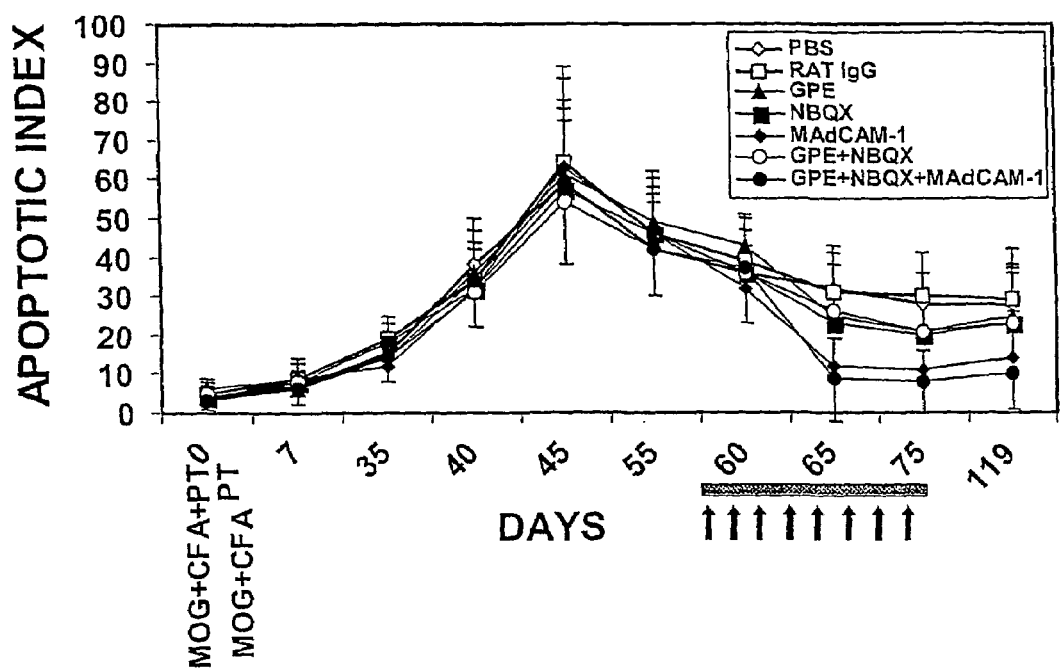
FIG. 3 shows apoptosis in the CNS, as assessed by TUNEL staining. Arrows refer to antibody administration, whereas the speckled line refers to neuroprotector administration.
Figure 4:
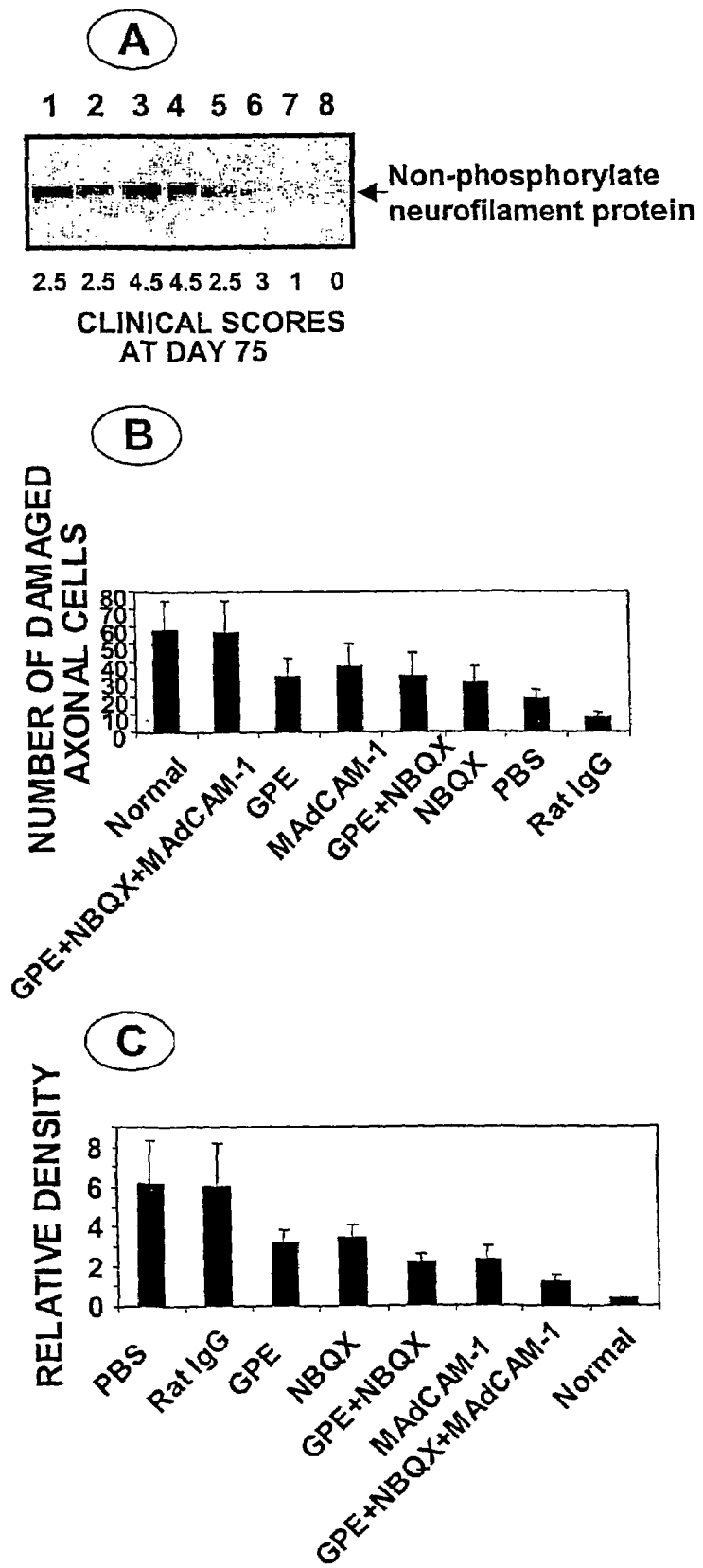
FIG. 4 shows the assessment of axonal damage by measuring levels of abnormally dephosphorylated neurofilament H. (A) Western blot analysis of dephosphorylated neurofilament H in spinal cord homogenates. PBS-perfused spinal cords were homogenized, and proteins Western blotted for dephosphorylated neurofilament H with the SM1-32 mAb. Immunoreactivity was detected by enhanced chemiluminescence and autoradiography. Homogenates were derived from mice treated with GPE (lane 1), NBQX (lane 2), PBS (lane 3), rat IgG (lane 4), GPE+NBQX (lane 5), anti-MAdCAM-1 mAb (lane 6), NBQX+GPE+anti-MAdCAM-1 mAb (lane 7), and from untreated normal mice (lane 8). Clinical scores at day 75 are indicated beneath the panel. (B) Numbers of damaged axonal cells. Numbers of cells staining for dephosphorylated neurofilament H. Data represent the means+s.e.m. (C) Densitometric analysis of Western blots of total spinal cord homogenate of 5 representative mice per group. Data represent the means+s.e.m.

Neuropathological evaluation confirmed the observed clinical protection achieved with the various treatment regimes. Spinal cord sections stained by TUNEL analysis revealed extensive apoptosis which peaked at the height of disease severity (day 49), and then subsequently declined slightly to reach a plateau that was maintained for the duration of the experiment (FIG. 3). Apoptotic cells were not identified but it is probable that infiltrating T cells, macrophages, and resident microglia and oligodendrocytes are all represented. Infiltrating T cells in particular appear to undergo apoptosis, as the body tries to clear autoimmune inflammation.

Sections taken from NBQX+GPE+anti-MAdCAM-1, and anti-MAdCAM-1 treated mice had substantial reductions (60%) in the numbers of apoptotic cells compared to mice that had been mock treated with either PBS or rat IgG. In contrast, sections taken from NBQX+GPE, NBQX, and GPE treated mice showed lesser reductions (~30%) in the number of apoptotic cells.

Axonal damage is a critical feature of multiple sclerosis lesions. Dephosphorylated heavy chain neurofilament-H is a quantitative molecular marker of demyelinated and dystrophic axons, and is employed to assess axonal damage and disease severity. Using both immunohistochemistry (FIG. 4B) and Western blot analysis (FIGS. 4A and C), it was revealed that the spinal cords of mock-treated EAE mice (disease score 4.5) displayed a large increase of abnormally dephosphorylated neurofilament-H, whereas normal undiseased mice had almost undetectable levels (FIGS. A and B). In accord these spinal cords also contained increased numbers of damaged axonal cells (FIG. 4B). Once again, the levels of dephosphorylated neurofilament-H, and numbers of damaged axonal cells correlated with the efficacy of the particular treatment regime. For example the average relative densities of neurofilament-H in spinal cord homogenates resolved by Western blot analysis were 1.2 for NBQX+GPE+anti-MAdCAM-1, 2.2 for NBQX+GPE, 2.3 for anti-MAdCAM-1, 3.2 for GPE, and 3.5 for NBQX, compared to 6.1 for either rat IgG or PBS treated control mice). This indicates that the triple combination was very effective in reducing axonal damage almost to background levels.

GPE and NBQX administered individually almost halved the amount of axonal damage, and in combination further reduced damage by 30%, indicating the involvement of glutamate excitotoxicity. Surprisingly, anti-MAdCAM-1 mAb treatment was almost as effective as the combination of GPE+NBQX, which correlated with its ability to reduce the apoptotic index (FIG. 3).

These results clearly indicate that the anti-inflammatory reagents and neuroprotectors used act in concert to reduce the degree of axonal damage, as reflected in the attenuation of clinical symptoms of disease.

Mechanisms Responsible for the Protective Effects of Combination Therapy

Figure 5:
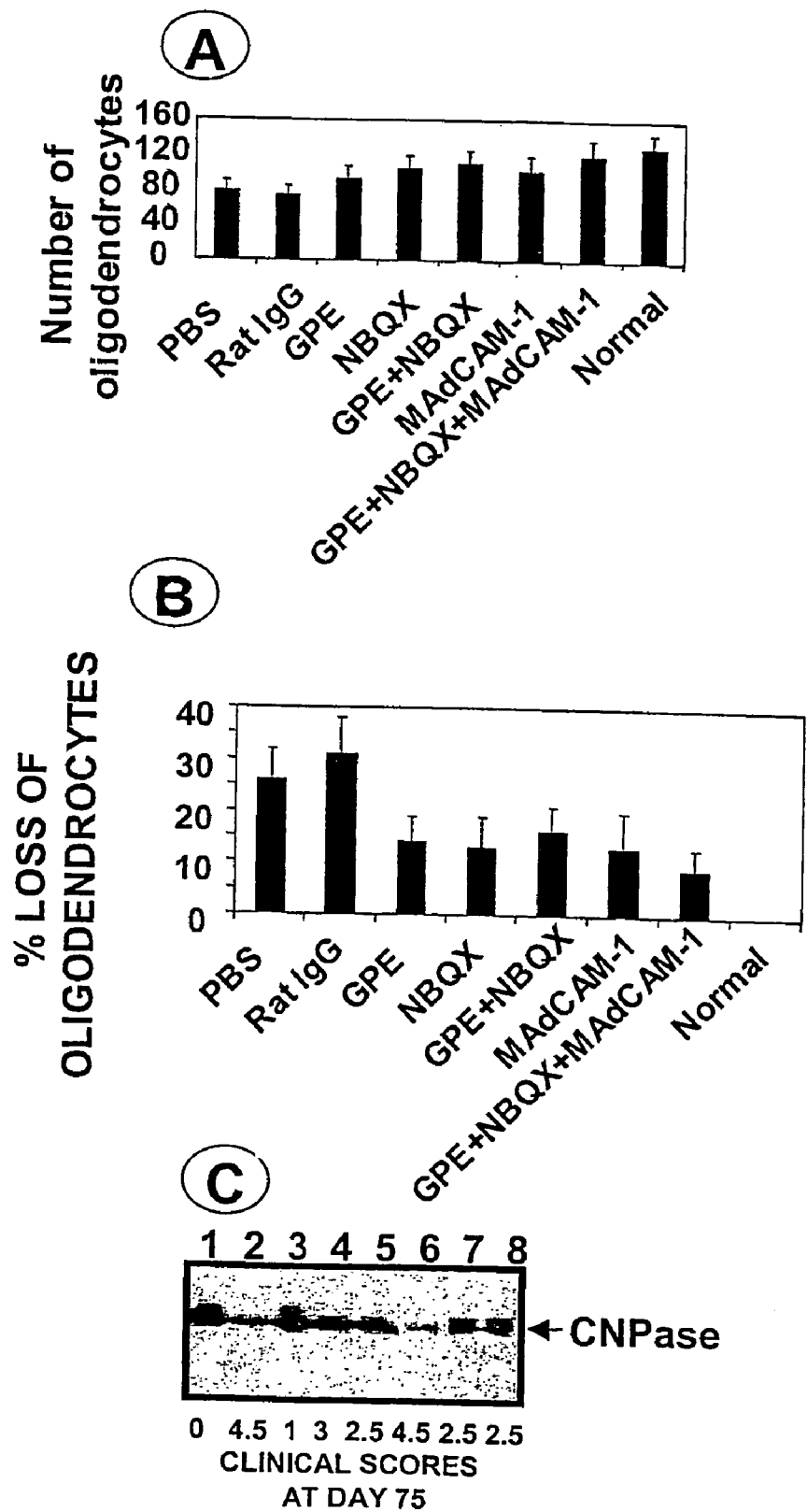
FIG. 5 shows oligodendrocyte survival from measurement CNPase-immunoreactivity. (A) Enumeration of oligodendrocytes in transverse sections of dorsal columns. Each bar represents the average number of oligodendrocytes from two representative mice, with 5–10 sections analyzed per mouse. (B) Oligodendrocyte loss in the CNS of treated versus mock treated and untreated mice. Data are expressed as the percentage+s.e.m. of cells lost per dorsal column. (C) Western blot analysis of CNPase in spinal cord homogenates. PBS-perfused spinal cords were homogenized, and proteins Western blotted with an anti-CNPase mAb. Immunoreactivity was detected by enhanced chemiluminescence and autoradiography. Homogenates were derived from normal undiseased mice (lane 1), and from EAE mice treated with PBS (lane 2), NBQX+GPE+anti-MAdCAM-1 mAb (lane 3), anti-MAdCAM-1 mAb (lane 4), GPE+NBQX (lane 5), rat IgG (lane 6), NBQX (lane 7), and GPE (lane 8). Clinical scores at day 75 are indicated beneath the panel.

To evaluate the effects of the different treatment regimes on the loss of oligodendrocytes, a key cellular target in demyelinating diseases of the CNS, oligodendrocytes were enumerated by immunohistochemical staining of spinal cord sections and the number of oligodendrocytes within the dorsal columns of x transverse sections were counted (FIG. 5B), and reductions in oligodendrocyte numbers were calculated and expressed as % loss of oligodendrocytes per dorsal section (FIG. 5C). The % loss of oligodendrocytes correlated with the efficacy of the different treatment regimes, such that the % loss was 9 for NBQX+GPE+anti-MAdCAM-1, 16 for NBQX+GPE, 13 for anti-MAdCAM-1, 14 for GPE, and 13 for NBQX, compared to 31 for rat IgG and 26 for PBS treated control mice. These results were confirmed by Western blot analysis to quantitate the amount of CNPase in spinal cord homogenates (FIG. 5D).

Figure 6:
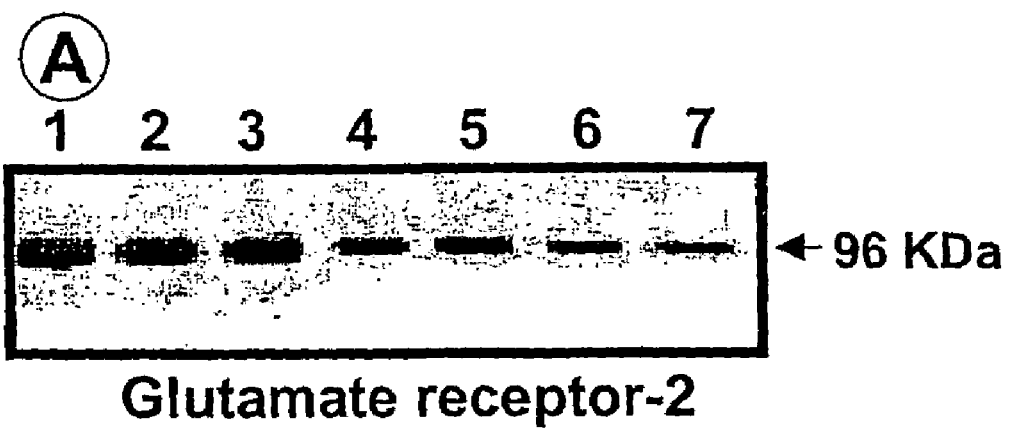
FIG. 6 shows that glutamate receptor subunit upregulation is blocked by therapy. (A) Western blot analysis of GluR2 subunit expression in spinal cord homogenates. PBS-perfused spinal cords were homogenized, and proteins Western blotted with an anti-GluR2 mAb. Homogenates were derived from mice treated with rat IgG (lane 1), GPE (lane 2), anti-MAdCAM-1 mAb (lane 3), NBQX+GPE+anti-MAdCAM-1 mAb (lane 4), GPE+NBQX (lane 5), NBQX (lane 6), and from normal mice (lane 7). (B) Western blot analysis of NMDAR1 subunit expression in spinal cord homogenates. PBS-perfused spinal cords were homogenized, and proteins Western blotted with an anti-NMDAR1 mAb. Homogenates were derived from normal undiseased mice (lane 1), and mice treated with treated with NBQX (lane 2), NBQX+GPE+anti-MAdCAM-1 mAb (lane 3), GPE+NBQX (lane 4), GPE (lane 5), anti-MAdCAM-1 mAb (lane 6), and PBS (lane 7). Immunoreactivity was detected by enhanced chemiluminescence and autoradiography.
Figure 6:
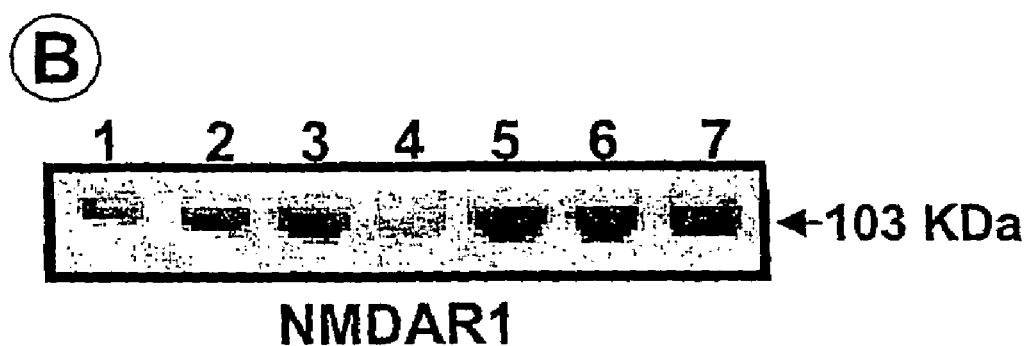

Levels of the AMPA receptor subunits GluR1 and 2 have been shown to increase in the rat spinal cord after inflammation, suggesting their upregulation is an indicator of disease (Zhou et al., 2001). Thus levels of GluR2 and the NMDA receptor subunit NR1 were determined in the current investigation. As shown by both immunohistochemical staining of spinal cord sections (FIG. 6A), and Western blot analysis of spinal cord homogenates (FIGS. 6B and C) there were marked increases in GluR2 and NR1 subunit expression in the spinal cords of mock-treated EAE mice. Treatments that included NBQX led to a marked down-regulation of GluR2 expression, whereas GPE and anti-MAdCAM-1 mAb reagents had negligible effect. Thus, NBQX either directly or indirectly downregulates the AMPA receptor following binding. Surprisingly, NBQX also caused down-regulation of the NMDA receptor, whereas anti-MAdCAM-1 mAb and GPE were not effective. This is in accord with a study showing that drug regimes targeting one ionotropic glutamate receptor subtype may indirectly affect other subtypes (Healy et al., 2000).

Figure 7:
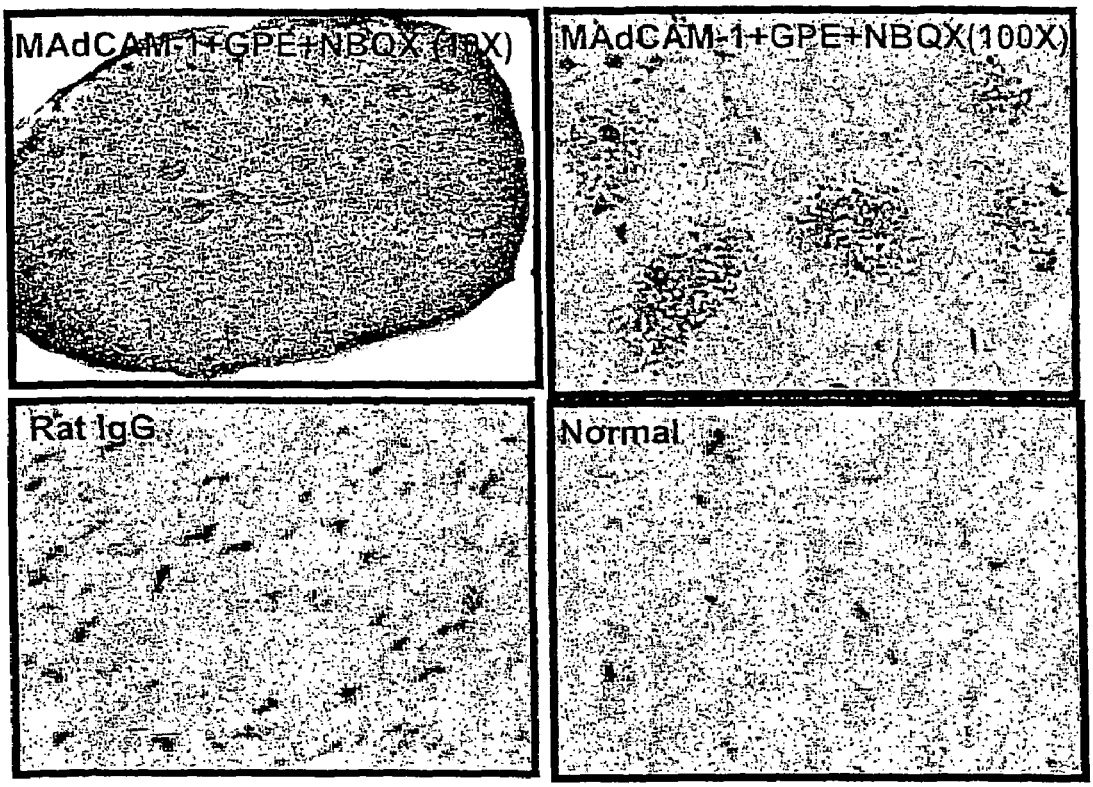
FIG. 7 shows the assessment of remyelination by staining for exon 2 of myelin basic protein (MBP). Transverse sections of the spinal cord were immunostained with a rabbit polyclonal antibody against exon 2 of MBP to visualize areas undergoing remyelination.

Sections were stained with a rabbit polyclonal antibody raised against a peptide containing exon 2 of MBP, to provide evidence of remyelination. Distinct patches in the spinal cord stained with the anti-exon 2 MBP antibody, where the number of stained patches correlated with the efficacy of each treatment regime (FIG. 7).

A score was given to each neuropathological parameter, based on the degree of CNS involvement (Table 2). The cumulative scores for inflammation, demyelination, remyelination, apoptosis, oligodendrocyte loss, and axonal damage following treatment correlated with the efficacy of the different treatment regimes, such that the score was 24 for NBQX+GPE+anti-MAdCAM-1, 40 for NBQX+GPE, 42 for anti-MAdCAM-1, 55 for GPE, and 46 for NBQX, compared to 46 for rat IgG and 58 for PBS treated control mice.

TABLE 2

Pathology status scale*.

| | Inflammation | | | | | Demyelination | | | | | Remyelination** | | | | | Apoptosis | | | | |
|---|---|---|---|---|---|---|---|---|---|---|---|---|---|---|---|---|---|---|---|---|
| | 45 | 60 | 65 | 70 | 119 | 45 | 60 | 65 | 70 | 119 | 45 | 60 | 65 | 70 | 119 | 45 | 60 | 65 | 70 | 119 |
| PBS | 3 | 3 | 2 | 2 | 2 | 3 | 2 | 2 | 1 | 2 | 3 | 3 | 2 | 2 | 2 | 3 | 2 | 2 | 1 | 2 |
| Rat IgG | 3 | 2 | 2 | 3 | 2 | 2 | 3 | 3 | 2 | 2 | 3 | 2 | 2 | 3 | 2 | 2 | 3 | 3 | 2 | 2 |
| GPE | 2 | 3 | 2 | 2 | 1 | 3 | 3 | 2 | 3 | 2 | 2 | 3 | 2 | 2 | 1 | 3 | 3 | 2 | 3 | 2 |
| NBQX | 3 | 3 | 2 | 2 | 1 | 2 | 3 | 2 | 1 | 2 | 3 | 2 | 2 | 2 | 1 | 2 | 3 | 2 | 1 | 2 |
| GPE + NBQX | 2 | 3 | 1 | 1 | 1 | 3 | 3 | 2 | 1 | 1 | 2 | 3 | 1 | 1 | 1 | 3 | 3 | 2 | 1 | 1 |
| MadCAM-1 | 3 | 3 | 1 | 0 | 1 | 3 | 3 | 2 | 2 | 1 | 3 | 3 | 1 | 0 | 1 | 2 | 3 | 2 | 2 | 1 |
| GPE + NBQX + MadCAM-1 | 3 | 3 | 0 | 0 | 1 | 3 | 3 | 1 | 0 | 0 | 3 | 3 | 0 | 0 | 1 | 3 | 3 | 1 | 0 | 0 |

| | Oligodendrocytes** | | | | | Axonal damage | | | | | Total scores After treatment |
|---|---|---|---|---|---|---|---|---|---|---|---|
| | 45 | 60 | 65 | 70 | 119 | 45 | 60 | 65 | 70 | 119 | |
| PBS | 3 | 2 | 2 | 1 | 2 | 3 | 2 | 2 | 1 | 2 | 46 |
| Rat IgG | 2 | 3 | 3 | 2 | 2 | 2 | 3 | 3 | 2 | 2 | 58 |
| GPE | 3 | 3 | 2 | 2 | 2 | 3 | 3 | 2 | 3 | 2 | 55 |
| NBQX | 2 | 3 | 2 | 1 | 2 | 2 | 3 | 1 | 1 | 2 | 46 |
| GPE + BQX | 3 | 3 | 2 | 1 | 1 | 3 | 3 | 2 | 1 | 1 | 40 |
| MadCA | 2 | 3 | 2 | 2 | 1 | 2 | 3 | 2 | 2 | 1 | 42 |

TABLE 2-continued

Pathology status scale*.

| Treatment | | | | | | | | | | | |
|---|---|---|---|---|---|---|---|---|---|---|---|
| M-1 GPE + N BQX + MadC AM-1 | 3 | 3 | 1 | 0 | 0 | 3 | 3 | 1 | 0 | 0 | 24 |

*Examples of scoring and averaging system in two selected animals were determined from two sections, read blindly, from each cord level.
**Reverse scores.

These results show anti-MAdCAM-1, GPE and NBQX monotherapies which either block inflammation, or glutamate excitotoxicity, or induce remyelination are preventative when administered early, prior to establishment of significant nerve damage.

Furthermore, the results indicate that blockade of MAdCAM-1 alone is able to prevent the early development of disease.

The results also show that effects of GPE and NBQX are synergistic (FIG. 1B). The combination of GPE and NBQX reduced the average clinical score, led to increased weight gain, and reduced the neuropathology in particular axonal damage, and loss of oligodendrocytes, compared to the respective monotherapies.

The results further show that the triple combination of NBQX+GPE+anti-MAdCAM-1 was the most efficacious approach, reducing the clinical, disability, and neuropathology scores almost to background levels. The weight of mice returned to normal, and there were few signs of axonal damage, paralysis, or disability.

Although the invention has been described with reference to particular embodiments, those persons skilled in the art will appreciate that variations and modifications may be made without departing from the scope of the invention.

REFERENCES

Baron, J. L., Madri, J. A., Ruddle, N. H., Hashim, G., Janeway, C. A. Jr., 1993. Surface expression of □4 integrin by CD4 T cells is required for their entry into brain parenchyma. J. Exp. Med. 177, 57–68.

Berg, R. W., Yang, Y., Lehnert, K., and Krissansen, G. W. Mouse M290 is the functional homologue of the human mucosal lymphocyte integrin HML-1: Antagonism between the integrin ligands E-cadherin and RGD tripeptide. Immunol. Cell Biol. 1999, 77: 337–344.

Berlin, C., Berg, E. L., Brislin, M. J., Andrew, D. P., Kilshaw, P. J., Holzmann, B., Weissman, I. L., Hamann, A., Butcher, E. C., 1993. α4β7 integrin mediates lymphocyte binding to the mucosal vascular addressin MAdCAM-1. Cell 74, 185–195.

Briskin, M. J., McEvoy, L. M., Butcher, E. C., 1993. MAdCAM-1 has homology to immunoglobulin and mucin-like adhesion receptors and to IgA1. Nature 363, 461–463.

Brosnan, C. F., Raine, C. S., 1996. Mechanisms of immune injury in multiple sclerosis. Brain Pathol. 6, 243–257.

Cannella, B., Raine, C. S., 1995. The adhesion molecule and cytokine profile of multiple sclerosis lesions. Ann. Neurol. 37, 424–435.

Cannella, B., Pitt, D., Capello, E., Raine C S. 2000. Insulin-like growth factor-1 fails to enhance central nervous system myelin repair during autoimmune demyelination. Am J Path. 157:933–943.

Carson, M. J., Behringer, R. R., Brinster, R. L., McMorris, F. A., 1993. Insulin-like growth factor I increases brain growth and central nervous system myelination in transgenic mice. Neuron 10, 729–740.

Cepek, K. L., Shaw, S. K., Parker, C. M., Russell, G. J., Morrow, J. S., Rimm, D. L., Brenner, M. B., 1994. Adhesion between epithelial cells and T lymphocytes mediated by E-cadherin and the αEβ7 integrin. Nature 372, 190–193.

Healy, D. J., Meador-Woodruff, J. H. 2000. Ionotropic glutamate receptor modulation preferentially affects NMDA receptor expression in rat hippocampus. Synapse 38: 294–304.

Holzmann, B., Weissman, I. L., 1989. Peyer's patch-specific lymphocyte homing receptors consist of a VLA-4-like a chain associated with either of two integrin β chains, one of which is novel. EMBO J. 8, 1735–1741.

Hwang et al., (1980) Hepatic uptake and degradation of unilamellar sphingomyelin/cholesterol liposomes: a kinetic study. Proc. of the Natl. Acad. of Sciences USA 77: 4030–4034.

Kanwar, J. R., Harrison, J. E. B., Wang, D., Leung, E., Wagner, N., Mueller, W., and Krissansen, G. W. Contributory role for β7 integrins in non-remitting experimental autoimmune encephalomyelitis. J. Neuroimmunol. 103: 146–152, 2000a.

Kanwar, J. R., Wang, D., and Krissansen, G. W. Prevention of a chronic progressive form of experimental autoimmune encephalomyelitis by an antibody against MAdCAM-1, given early in the course of disease progression. Immunol. Cell Biol.78: 641–646, 2000b.

Karecla, P. I., Bowden, S. J., Green, S. J., Kilshaw, P. J., 1995. Recognition of E-cadherin on epithelial cells by the mucosal T cell integrin aM290b7 (αEβ7). Eur. J. Immunol. 25, 852–856.

Klempt N D, Sirimanne E, Gunn A J, Klempt M, Singh K, Williams C, Gluckman P D, 1992. Hypoxia-ischemia induces transforming growth factor β1 mRNA in the infant rat brain. Molecular Brain Research: 13: 93–101.

Krissansen, G. W., Print, C. G., Prestidge, R. L., Hollander, D., Yuan, Q., Jiang, W-M., Jenkins, D. R., Leung, E., Mead, P., Yong, R., Ameratunga, R. V., Cerf-Bensussan, N., Watson, J. D., 1992. Immunologic and structural relatedness of the integrin β7 complex and the human intraepithelial lymphocyte antigen HML-1. FEBS Lett. 296, 25–28.

Langer et al., 1981. Biocompatibility of polymeric delivery systems for macromolecules. J. Biomed. Mater. Res. 15: 267–277.

Martin, R., McFarland, H. F., 1995. Immunological aspects of experimental allergic encephalomyelitis and multiple sclerosis. Critical Rev. Clin. Lab. Sci. 32, 121–182.

McDonald, J. W., Althomsons, S. P., Hyrc, K. L., Choi, D. W., and Goldberg, M. P., 1998. Oligodendrocytes from forebrain are highly vulnerable to AMPA/kainate receptor-mediated excitotoxicity. Nature Med. 4, 291–297.

Mendel, I., Kerlero de Rosbo, N., Ben-Nun, A., 1995. A myelin oligodendrocyte glycoprotein peptide induces typical chronic experimental autoimmune encephalomyelitis in H-2b mice: fine specificity and T cell receptor V beta expression of encephalitogenic T cells. Eur. J. Immunol. 25, 1951–1959.

Moore, G. R. W., Traugott, U., Farooq, M., Norton, W. T., Raine, C. S. 1984 Experimental autoimmune encephalomyelitis: Augmentation of demyelination by different myelin lipids. Lab Invest. 51:416–424.

Parker, C. M., Cepek, K. L., Russell, G. J., Shaw, S. K., Posnett, D. N., Schwarting, R., Brenner, M. B., 1992. A family of β7 integrins on human mucosal lymphocytes. Proc. Natl. Acad. Sci. USA 89, 1924–1928.

Peterson G L. 1983. Determination of total protein. Methods Enzymol. 91:95–119.

Pitt, D., Werner, P., Raine, C. S., 2000. Glutamate excitotoxicity in a model of multiple sclerosis. Nature Med. 6, 67–70.

Raine, C. S., 1991. Multiple sclerosis: a pivotal role for the T cell in lesion development. Neuropath. Applied Neurobiol. 17, 265–274.

Raine, C. S., 1994. The Dale E. McFarlin Memorial Lecture: the immunology of the multiple sclerosis lesion. Ann. Neurol. 36, S61–72.

Saura, J., Curatolo, L., Williams, C. E., Gatti, S., Benatti, L., Peeters, C., Guan, J., Dragunow, M., Post, C., Faull, R. L. M., Gluckman, P. D., Skinner, S. J. M., 1999. Neuroprotective effects of Gly-Pro-Glu, the N-terminal tripeptide of IGF-1, in the hippocampus in vitro. NeuroReport 10, 161–164.

Selmaj, K., Walczak, A., Mycko, M., Berkowicz, T., Kohno, T., Raine, C. S., 1998. Suppression of experimental autoimmune encephalomyelitis with a TNF binding protein (TNFbp) correlates with down-regulation of VCAM-1/VLA-4. Eur. J. Immunol. 28, 2035–2044.

Sidman et al., 1983. Controlled release of macromolecules and pharmaceuticals from synthetic polypeptides based on glutamic acid. Biopolymers 22, 547–556.

Smith, T., Groom, A., Zhu, B., Turski, L., 2000. Autoimmune encephalomyelitis ameliorated by AMPA antagonists. Nature Med. 6, 62–66.

Stover, J. F. et al., 1997. Neurotransmitters in cerebrospinal fluid reflect pathological activity. Eur. J. Clin. Invest. 27, 1038–1043.

Streeter, P. R., Berg, E. L., Rouse, B. T., Bargatze, R. F., Butcher E C., 1988. A tissue-specific endothelial cell molecule involved in lymphocyte homing. Nature. 331, 41–46.

Szabo, M. C., Butcher, E. C., McEvoy, L. M., 1997. Specialization of mucosal follicular dendritic cells revealed by mucosal addressin-cell adhesion molecule-1 display. J. Immunol. 158, 5584–5588.

Tapson, V. F., Boni-Schnetzler, M., Pilch, P. F., Center, D. M., Berman, J. S., 1988. Structural and functional characterization of the human T lymphocyte receptor for insulin-like growth factor I in vitro. J. Clin. Invest. 82, 950–957.

Tubridy, N., Behan, P O., Capildeo, R., Chaudhuri, A., Forbes, R., Hawkins, C. P., Hughes, R. A., Palace, J., Sharrack, B., Swingler, R., Young, C., Moseley, I. F., MacManus, D. G., Donoghue, S., Miller, D. H., 1999. The effect of anti-alpha4 integrin antibody on brain lesion activity in MS. The UK Antegren Study Group. Neurol. 53:466–72.

Villoslada, P., Hauser, S. L., Bartke, I., Unger, J., Heald, N., Rosenberg, D., Cheung, S. W., Mobley, W. C., Fisher, S., Genain, C. P. 2000. Human nerve growth factor protects common marmosets against autoimmune encephalomyelitis by switching the balance of T helper cell type 1 and 2 cytolines within the central nervous system. J Exp Med 191:1799–806.

Wagner, N., Lohler, J., Kunkel, E. J., Ley, K., Leung, E., Krissansen, G., Rajewsky, K., Muller, W., 1996. Critical role for β7 integrins in the formation of the gut associated lymphoid tissue. Nature 382, 366–370.

Yang, X., Sytwn, H-K., McDevitt, H. O., Michie, S. A., 1997. Involvement of β7 integrin and mucosal addressin cell adhesion molecule-1 (MAdCAM-1) in the development of diabetes in nonobese diabetic mice. Diabetes 46, 1542–1547.

Yang, Y., Sammar, M., Harrison, J. E. B., Lehnert, K., Print, C. G., Leung, E., Prestidge, R., Krissansen, G. W., 1995. Construction and adhesive properties of a soluble MAd-CAM-1-Fc chimera expressed in a baculovirus system: phylogenetic conservation of receptor-ligand interaction. Scand. J. Immunol. 42, 235–247.

Yednock, T. A., Cannon, C., Fritz, L. C., Sanchez-Madrid, F., Steinman, L., Karin, N., 1992. Prevention of experimental autoimmune encephalomyelitis by antibodies against α4β1 integrin. Nature 356, 63–66.

Yuan, Q., Jiang, W-M., Leung, E., Hollander, D., Watson, J. D., Krissansen, G. W., 1992. Molecular cloning of the mouse integrin β7 subunit. J.Biol.Chem. 267, 7352–7358.

Zhou, Q. Q., Imbe, H., Zou, S., Dubner, R., Ren, K. 2001. Selective upregulation of the flip-flop splice variants of AMPA receptor subunits in the rat spinal cord after hindpaw inflammation. Brain Res. Mol. Brain Res. 88: 186–193.

The invention claimed is:

1. A method of treating degeneration of white matter and death of oligodendrocytes and axons in a mammal resulting from a demyelinating disease comprising the step of administering to said mammal a neuroprotective amount of the tripeptide gly-pro-glu (GPE) or a pharmaceutically acceptable salt thereof, in combination with an α-amino-3-hydroxy-5-methyl-4-isoxazolepropionate/kainate antagonist or a pharmaceutically acceptable salt thereof and an anti-inflammatory agent.

2. The method of claim 1, wherein the α-amino-3-hydroxy-5-methyl-4-isoxazolepropionate/kainate antagonist is selected from the group consisting of 2,3-dihydroxy-6-nitro-7-sulfamoylbenzo(F)quinoxaline (NBOX), 1,2,3,4-tetrahydro-7-morpholinyl-2,3-dioxo-6-(trifluoromethyl)quinoxalin-1-yl]methylphosphonate, 1-(4-aminophenyl)-4-methyl-7,8-methylenedioxy-5H-2,3-benzodiazepine, (−)1-(4-aminophenyl)-4-methyl-7,8-methylene-dioxy-4,5-dihydro-3-methylcarbamoyl-2,3-benzodiazepine, D(−)-2 amino 4 phosphobutyric acid,-6,7-dimitroquinoxaline-2,3-dione, 6-cyano-7-nitroquinoxaline-2,3,-dione, (3S,4aR,6R,8aR)-6-[2-(1(2)H-tetrazole-5-yl)]decahydroiso quinoline-3-carboxylic acid, 1-(4'aminophenyl)-3,5-dihydro-7,8-dimethoxy-4H-2,3-benzodiazepin-4-one, γ-D-glutamylaminomethyl suphonic acid and (±)-4-(4-Aminophenyl)-1,2-dihydro-1-methyl-2-propylcarbmoyl-6,7-methylenedioxyphthalazine, [$^3$H]9-imidazol-1-yl-8-nitro-2,3,5,6-tetrahydro-(1,2,4)-triazolo-(1,5-c)-quinazoline-2,5-dione], 6-(1H-imidazol-1-yl)-7-nitro-2,3-(1H,4H)-quinoxalineclione, 1,4,7,8,9,10-hexahydro-9-methyl-6-nitropyrido[3,4-f]quinoxaline-2,3-dione, or a pharmaceutically acceptable salt thereof.

3. The method of claim 1, wherein the α-amino-3-hydroxy-5-methyl-4-isoxazolepropionate/kainate antagonist is 2,3-dihydroxy-6-nitro-7-sulfamoylbenzo(F)quinoxaline or a pharmaceutically acceptable salt thereof.

4. The method of claim 1, wherein the anti-inflammatory agent is an antibody directed against mucosal addressin cell adhesion molecule-1 (MAdCAM-1) and/or its integrin α4 receptors (α4β1 and α4β7).

5. The method of claim 1, wherein the anti-inflammatory agent is selected from the group consisting of anti-integrin alpha4 subunit reagents, anti-integrin beta 7 subunit reagents, anti-integrin beta 2 subunit reagents, anti-integrin alpha L subunit reagents, anti-MAdCAM-1, anti-VCAM-1 reagents and anti-ICAM-1 reagents.

6. The method of claim 1, wherein the administration occurs before an insult.

7. The method of claim 1, wherein the administration occurs after an insult.

8. The method of claim 1, wherein the insult is selected from acute or chronic encephalomyelitis, optic neuritis, transverse myelitis, Devic's disease, the leucodystrophies, multiple sclerosis, progressive multifocal leukoencephalopathy, central pontine myelinolysis, neuromyelitits optica, diffuse cerebral sclerosis of Schilder, acute and subacute necrotizing haemorrhagic encephalitis.

9. The method of claim 1, wherein the demyelinating disease is multiple sclerosis.

10. A method of protection from degeneration of white matter and death of oligodendrocytes and axons in a mammal resulting from a demyelinating disease comprising the step of increasing the active concentration of the tripeptide gly-pro-glu (GPE) or a pharmaceutically acceptable salt thereof in combination with increasing the active concentration of an α-amino-3-hydroxy-5-methyl-4-isoxazolepropionate/kainate antagonist or a pharmaceutically acceptable salt thereof and an anti inflammatory agent, in a mammal in need hereof.

11. The method of claim 10, wherein the administration occurs before an insult.

12. The method of claim 10, wherein the administration occurs after an insult.

13. The method of claim 1 comprising the administration in the form of a pharmaceutical composition including a pharmaceutically acceptable carrier therefor.

14. The method of claim 1 comprising the administration directly to where the white matter, axons and oligodendrocytes to be protected are located.

15. The method of claim 1 comprising the administration directly to the brain or cerebrospinal fluid by cerebroventricular injection, by injection into the cerebral parenchyma or through a surgically inserted shunt into the lateral cerebral ventricle of the brain.

16. The method of claim 1 comprising the administration by cerebroventricular injection.

17. The method of claim 1 comprising the administration in combination with artificial cerebrospinal fluid.

18. The method of claim 1 comprising the administration systemically for transport to where the white matter, axons and oligodendrocytes to be protected are located.

19. The method of claim 1 comprising the administration through an intravenous, oral, rectal, nasal, subcutaneous, inhalation, intraperitoneal or intramuscular route.

20. The method of claim 1 comprising the administration by intraperitoneal injection.

21. The method of claim 1, wherein a dosage range administered is from about-1 µg to about-100 mg of GPE or a pharmaceutically acceptable salt thereof per kg of body weight of the mammal.

22. The method of claim 1, wherein a dosage range administered is from about 60 µg to about 600 mg of 2,3-dihydroxy-6-nitro-7-sulfamoylbenzo(F)quinoxaline or a pharmaceutically acceptable salt thereof per kg of body weight of the mammal.

23. The method of claim 1, wherein a dosage administered is from about 30 µg to about 300 mg of anti MAdCAM-1 antibody per kg of body weight of the mammal.

24. A therapeutic kit for the treating a demyelinating disease of the CNS comprising GPE or a pharmaceutically acceptable salt thereof and an amino-3-hydroxy-5-methyl-4-isoxazolepropionate/kainate antagonist or a pharmaceutically acceptable salt thereof and an anti-inflammatory agent.

25. A therapeutic kit for the treating a demyelinating disease of the CNS comprising GPE or a pharmaceutically acceptable salt thereof and 2,3-dihydroxy-6-nitro-7-sulfamoylbenzo(F)quinoxaline or a pharmaceutically acceptable salt thereof and an antibody directed against MAdCAM-1 and/or its integrin α4 receptors (α4β1 and α4β7).

26. A method for manufacturing a pharmaceutically composition, comprising: combining a neuroprotective amount of the tripeptide gly-pro-glu (GPE) or a pharmaceutically acceptable salt thereof, an α-amino-3-hydroxy-5-methyl-4-isoxazolepropionate/kainate antagonist or a pharmaceutically acceptable salt thereof, and an anti-inflammatory agent.

27. The method of claim 26, wherein the a amino-3 hydroxy-5 methyl 4isoxazolepropionate/kainate antagonist is selected from the group consisting of 2,3-dihydroxy-6-nitro-7-sulfamoylbenzo(F)quinoxaline, 1,2,3,4-tetrahydro-7-morpholinyl-2,3-dioxo-6-(trifluoromethyl)quinoxalin-1-yl]methylphosphonate, 1-(4-aminophenyl)-4-methyl-7,8-methylenedioxy-5H-2,3-benzodiazepine, (−)1-(4-aminophenyl)-4-methyl-7,8-methylene-dioxy-4,5-dihydro-3-methylcarbamoyl-2,3-benzodiazepine, D(−)-2-amino-4-phosphobutyric acid, 6,7-dinitroquinoxaline-2,3-dione, 6-cyano-7-nitroquinoxaline-2,3,-dione, (3S,4aR,6R,8aR)-6-[2(1(2)H-tetrazole-5-yl)]decahydroiso quinoline-3-carboxylic acid, 1-(4'aminophenyl)-3,5-dihydro-7,8-dimethoxy-4H-2,3-benzodiazepin-4-one, γ-D-glutamylaminomethyl suphonic acid and (±)-4-(4-Aminophenyl)-1,2-dihydro-1-methyl2-propylcarbamoyl-6,7-methylenedioxyphthalazine, [$^3$H]9-imidazol-1-yl-8-nitro-2,3,5,6-tetrahydro-(1,2,4)-triazolo-(1,5-c) -quinazoline-2,5-dione], 6-(1H-imidazol-1-yl)-7-nitro-2,3-(1H,4H)-quinoxalinedione-1,4,7,8,9,10-hexahydro-9-methyl6-nitropyrido[3,4-f]quinoxaline-2,3 dione, or a pharmaceutically acceptable salt thereof.

28. The method of claim 26, wherein the α-amino-3 hydroxy-5-methyl-4-isoxazolepropionate/kainate antagonist is 2,3-dihydroxy-6-nitro-7-sulfamoylbenzo(F)quinoxaline or a pharmaceutically acceptable salt thereof.

29. The method of claim 26, wherein the anti inflammatory agent is an antibody directed against MAdCAM-1 and/or its integrin α4 receptors (α4β1 and α4β7).

30. The method of claim 26, wherein the anti inflammatory agent is selected from the group consisting of anti-integrin alpha 4 subunit reagents, anti-integrin beta 7 subunit reagents, anti-integrin beta 2 subunit reagents, anti-integrin alpha L subunit reagents, anti-MAdCAM-1, anti-VCAM-1 reagents and anti-ICAM-1 reagents.

31. The method of claim 7, wherein the insult is selected from acute or chronic encephalomyelitis, optic neuritis, transverse myelitis, Devic's disease, the leucodystrophies, multiple sclerosis, progressive multifocal leukoencephalopathy, central pontine myelinolysis, neuromyelitits optica, diffuse cerebral sclerosis of Schilder, acute and subacute necrotizing haemorrhagic encephalitis.

32. A method or protection from degeneration of white matter and death of oligodendrocytes and axons in a mammal resulting from a demyelinating disease comprising: administering to said animal an effective concentration of the tripeptide gly-pro-glu (GPE) or a pharmaceutically acceptable salt thereof; increasing the active concentration of an α-amino-3-hydroxy-5-methyl-4-isoxazolepropionate/kainate antagonist or a pharmaceutically acceptable salt thereof and administering an anti-inflammatory agent.

33. A method for protection from degeneration of white matter and death of oligodendrocytes and axons in a mammal resulting from a demyelinating disease, comprising administering to said animal a neuroprotective amount of the tripeptide gly-pro-glu (GPE) or a pharmaceutically acceptable salt thereof, in combination with an α-amino-3-hydroxy-5-methyl-4-isoxazolepropionate/kainate inhibitors or pharmaceutically acceptable salts thereof and an anti inflammatory agent.

34. The method of claim 33, wherein the administration is before an insult.

35. The method of claim 33, wherein the administration is after an insult.

36. The method of claim 33, wherein the administration is in the form of a pharmaceutical composition including a pharmaceutically acceptable carrier therefor.

37. The method of claim 33, wherein the administration is directly to where the white matter, axons and oligodendrocytes to be protected are located.

38. The method of claim 33, wherein the administration is directly to the brain or cerebrospinal fluid by cerebroventricular injection, by injection into the cerebral parenchyma or through a surgically inserted shunt into the lateral cerebral ventricle of the brain.

39. The method of claim 33, wherein the administration is by cerebroventricular injection.

40. The method of claim 33, wherein the administration is inn combination with artificial cerebrospinal fluid.

41. The method of claim 33, wherein the administration is systemically for transport to where the white matter, axons and oligodendrocytes to be protected are located.

42. The method of claim 33, wherein the administration is trough an intravenous, oral, rectal, nasal, subcutaneous, inhalation, intraperitoneal or intramuscular route.

43. The method of claim 33, wherein the administration is by intraperitoneal injection.

44. The method of claim 33, wherein a dosage range administered is from about-1 µg to about-100 mg of GPE or a pharmaceutically acceptable salt thereof per kg of body weight of the mammal.

45. The method of claim 33, wherein a dosage range administered is from about 60 µg to about 600 mg of 2,3-dihydroxy-6-nitro-7-sulfamoylbenzo(F)quinoxaline or a pharmaceutically acceptable salt thereof per kg of body weight of the mammal.

46. The method of claim 33, wherein a dosage range administered is from about 30 μg to about 300 mg of anti-MAdCAM-1 antibody per kg of body weight of the mammal.

47. A pharmaceutical composition comprising a therapeutically effective amount of the tripeptide gly-pro-glu (GPE) or a pharmaceutically acceptable salt thereof, in combination with an α-amino-3-hydroxy-5-methyl-4-isoxazolepropionate/kainate antagonist or a pharmaceutically acceptable' salt thereof and an anti inflammatory agent and a pharmaceutically acceptable excipient for the treatment of degeneration of white matter and death of oligodendrocytes and axons in a mammal resulting from a demyelinating disease.

48. A composition comprising GPE or a pharmaceutically acceptable salt thereof and an amino-3-hydroxy-5-methyl-4-isoxazolepropionate/kainate antagonist or a pharmaceutically acceptable salt thereof.

49. A method of treating degeneration of white matter and death of oligodendrocytes and axons in a mammal resulting from a demyelinating disease comprising the step of administering to said mammal a neuroprotective amount of the tripeptide gly-pro-glu (GPE) or a pharmaceutically acceptable salt thereof, in combination with an α-amino-3-hydroxy-5-methyl-4-isoxazolepropionate/kainate antagonist or a pharmaceutically acceptable salt thereof.

\* \* \* \* \*

UNITED STATES PATENT AND TRADEMARK OFFICE
CERTIFICATE OF CORRECTION

PATENT NO. : 7,192,931 B2
APPLICATION NO. : 10/398876
DATED : March 20, 2007
INVENTOR(S) : Krissansen et al.

It is certified that error appears in the above-identified patent and that said Letters Patent is hereby corrected as shown below:

Claim 26, Col. 23, line 33, after "a" and before "composition" delete "pharmaceutically" and insert --pharmaceutical--.

Claim 27, Col. 23, line 40, after "the" and before "amino-3" replace "a" with --α- --.

Claim 27, Col. 23, line 59, replace "methyl 6-nitro" with --methyl-6-nitro--.

Claim 32, Col. 24, line 17, after "said" and before "an" delete "animal" and insert --mammal--.

Claim 33, Col. 24, line 26, after "said" and before "a" delete "animal" and insert --mammal--.

Claim 33, Col. 24, line 29, after "kainate" and before "or" delete "inhibitors" and insert --inhibitor--.

Claim 40, Col. 24, line 50, before "combination" delete "inn" and insert --in--.

Claim 42, Col. 24, line 55, before "an" delete "trough" and insert --through--.

Claim 47, Col. 25, line 9, after "acceptable" delete " ' ".

Signed and Sealed this

Fourth Day of March, 2008

JON W. DUDAS
*Director of the United States Patent and Trademark Office*

SEQUENCE LISTING

<160> NUMBER OF SEQ ID NOS: 2

<210> SEQ ID NO 1
<211> LENGTH: 21
<212> TYPE: PRT
<213> ORGANISM: Homo sapiens

<400> SEQUENCE: 1

Met Glu Val Gly Trp Tyr Arg Ser Pro Phe Ser Arg Val Val His Leu
1               5                   10                  15

```
Tyr Arg Asn Gly Lys
            20

<210> SEQ ID NO 2
<211> LENGTH: 35
<212> TYPE: PRT
<213> ORGANISM: Homo sapiens

<400> SEQUENCE: 2

Asp Ser His Thr Arg Thr Thr His Tyr Gly Ser Leu Pro Gln Lys Ser
1               5                   10                  15

Gln His Gly Arg Thr Gln Asp Glu Asn Pro Val Val His Phe Phe Lys
            20                  25                  30

Asn Cys Gly
            35
```